United States Patent
Bluchel et al.

(10) Patent No.: US 11,458,235 B2
(45) Date of Patent: Oct. 4, 2022

(54) SORBENT FOR A DIALYSIS DEVICE AND DIALYSIS SYSTEM

(71) Applicants: TEMASEK POLYTECHNIC, Singapore (SG); AWAK TECHNOLOGIES PTE LTD, Singapore (SG)

(72) Inventors: Christian Gert Bluchel, Singapore (SG); Peter Haywood, Singapore (SG)

(73) Assignees: TEMASEK POLYTECHNIC, Singapore (SG); AWAK TECHNOLOGIES PTE LTD, Singapore (SG)

(*) Notice: Subject to any disclaimer, the term of this patent is extended or adjusted under 35 U.S.C. 154(b) by 513 days.

(21) Appl. No.: 16/466,138

(22) PCT Filed: Dec. 5, 2017

(86) PCT No.: PCT/SG2017/050599
§ 371 (c)(1),
(2) Date: Jun. 3, 2019

(87) PCT Pub. No.: WO2018/106185
PCT Pub. Date: Jun. 14, 2018

(65) Prior Publication Data
US 2020/0078507 A1    Mar. 12, 2020

(30) Foreign Application Priority Data
Dec. 5, 2016    (SG) .............................. 10201610175P

(51) Int. Cl.
*A61M 1/16*    (2006.01)
*B01J 39/17*    (2017.01)
(Continued)

(52) U.S. Cl.
CPC ........... *A61M 1/1696* (2013.01); *B01D 15/08* (2013.01); *B01J 20/0211* (2013.01); *B01J 20/20* (2013.01);
(Continued)

(58) Field of Classification Search
CPC ........ A61M 1/1696; A61M 2202/0057; A61M 2205/02; B01J 20/0211; B01J 20/20;
(Continued)

(56) References Cited

U.S. PATENT DOCUMENTS 3,850,835 A    11/1974   Marantz et al.
4,256,718 A     3/1981   McArthur et al.
(Continued)

FOREIGN PATENT DOCUMENTS

CN    105992599    10/2014
CN    104168934    11/2014
(Continued)

OTHER PUBLICATIONS

China Office Action for related Application No. 201780075463.6 dated Apr. 30, 2021.
(Continued)

*Primary Examiner* — John Kim
(74) *Attorney, Agent, or Firm* — Thomas | Horstemeyer, LLP

(57) ABSTRACT

The invention relates to a sorbent for removing metabolic waste products from a dialysis liquid, the sorbent comprising a soluble source of sodium ions. The sorbent comprises an ion exchange system which converts urea to ammonium ions and which is configured to exchange ammonium ions for predominantly hydrogen ions and to exchange Ca, Mg, and K for predominantly sodium ions. The soluble source of sodium ions overcomes an initial drop in sodium concentration in regenerated dialysate. When used in conjunction
(Continued)

with an infusion system configured to utilise exchange of Ca, Mg and K for sodium during dialysate regeneration a desired sodium ion concentration can be maintained.

8 Claims, 8 Drawing Sheets

(51) Int. Cl.
| | |
|---|---|
| *B01J 20/02* | (2006.01) |
| *B01J 20/24* | (2006.01) |
| *B01J 47/02* | (2017.01) |
| *B01J 47/04* | (2006.01) |
| *B01J 20/20* | (2006.01) |
| *B01J 39/12* | (2006.01) |
| *B01J 41/10* | (2006.01) |
| *B01D 15/08* | (2006.01) |
| *B01J 47/024* | (2017.01) |

(52) U.S. Cl.
CPC ............. *B01J 20/24* (2013.01); *B01J 39/12* (2013.01); *B01J 39/17* (2017.01); *B01J 41/10* (2013.01); *B01J 47/024* (2013.01); *B01J 47/04* (2013.01); *A61M 2202/0057* (2013.01); *A61M 2205/02* (2013.01); *B01J 2220/42* (2013.01); *B01J 2220/46* (2013.01); *B01J 2220/62* (2013.01)

(58) Field of Classification Search
CPC ... B01J 20/24; B01J 39/12; B01J 39/17; B01J 47/024; B01J 47/04; B01J 41/10; B01J 2220/62; B01J 2220/42; B01J 2220/46; B01D 15/08

See application file for complete search history.

(56) References Cited

U.S. PATENT DOCUMENTS

| | | |
|---|---|---|
| 6,627,164 B1 | 9/2003 | Wong |
| 6,818,196 B2 | 11/2004 | Wong |
| 7,241,272 B2 | 7/2007 | Karoor et al. |
| 8,580,112 B2 | 11/2013 | Updyke et al. |
| 8,647,506 B2 | 2/2014 | Wong |
| 2010/0078387 A1 | 4/2010 | Wong |
| 2011/0171713 A1 | 7/2011 | Bluchel et al. |
| 2013/0199998 A1 | 8/2013 | Kelly et al. |
| 2013/0213890 A1 | 8/2013 | Kelly et al. |
| 2013/0213891 A1 | 8/2013 | Karoor |
| 2014/0217028 A1 | 8/2014 | Pudil et al. |
| 2015/0144542 A1 | 5/2015 | Pudil et al. |
| 2015/0258266 A1 | 9/2015 | Merchant et al. |
| 2021/0205522 A1 | 7/2021 | Bluchel et al. |

FOREIGN PATENT DOCUMENTS

| | | |
|---|---|---|
| JP | S5819265 A | 2/1983 |
| WO | 0243859 | 6/2002 |
| WO | 2003041764 | 5/2003 |
| WO | 2005123230 | 12/2005 |
| WO | 2007103411 | 9/2007 |
| WO | 2009157877 | 12/2009 |
| WO | 2010141949 A2 | 12/2010 |
| WO | 2011102807 | 8/2011 |
| WO | 2013025844 A2 | 2/2013 |
| WO | 2015142624 A1 | 9/2015 |

OTHER PUBLICATIONS

International Search Report and Written Opinion dated Jul. 10, 2018 (PCT/SG2017/050599).
Japanese Office Action for related Application No. 2019-529958 dated Oct. 28, 2021.
International Preliminary Report on Patentability dated Apr. 11, 2019 (PCT/SG2017/050599).
International Search Report and Written Opinion dated Jun. 26, 2018 (PCT/SG2017/050599).
Russian Office Action for RU Patent Application No. 2019117530/14(033530) dated Dec. 13, 2021.
Further Written Opinion of the International Preliminary Examining Authority in PCT/SG2017/050599 dated Dec. 20, 2018.
Russia Office Action for related application No. 2019117530 dated Apr. 6, 2022.

SORBENT FOR A DIALYSIS DEVICE AND DIALYSIS SYSTEM

CROSS-REFERENCE TO RELATED APPLICATION

This application is the 35 U.S.C. § 371 national stage application of PCT Application No. PCT/SG2017/050599, filed on Dec. 5, 2017, and entitled "SORBENT FOR A DIALYSIS DEVICE AND DIALYSYS SYSTEM," which claims priority to and the benefit of SG Patent Application No. 10201610175P, filed on Dec. 5, 2016. The entire content of both of these applications is incorporated by reference herein.

FIELD OF INVENTION

The present invention relates to a sorbent for dialysis as well as to a sorbent system for regenerative dialysis which may be, but is not limited to, haemodialysis, peritoneal dialysis, liver dialysis, lung dialysis, water purification and regeneration of biological fluids.

BACKGROUND

The listing or discussion of an apparently prior-published document in this specification should not necessarily be taken as an acknowledgement that the document is part of the state of the art or is common general knowledge.

Dialysis is the separation of particles in a liquid on the basis of differences in their ability to pass through a membrane. In medicine, the term refers to the clinical purification of blood as a substitute for the normal function of the kidney. In particular, dialysis is used to replace kidney function for patients suffering from renal dysfunction or failure. The term may also refer to the purification of other biological fluids including ascites, urine, and haemofiltrate. The purification is typically done by contacting a biological fluid, such as blood, with a purifying liquid, such as dialysate, through a semipermeable membrane. This process removes excess water, electrolytes and waste toxins from the body, therefore ensuring their concentrations are within physiological ranges. Most commonly, the purifying fluid (typically dialysate) is only used one single time, and is simply discarded as "spent dialysis fluid" after it has contacted the biological fluid (typically blood) once. This is referred to as "single-pass" dialysis. Sorbent-based regenerative dialysis, on the other hand, is a process that recycles a dialysis fluid after it has been used to purify a biological fluid. The process removes unwanted substances from the spent dialysis fluid (regeneration) and replaces desired substances (reconstitution) to produce a "fresh dialysis fluid", which is then contacted again with the biological fluid to continue the dialysis process.

The predominant form of dialysis used for patients with end-stage renal disease is in-centre single-pass haemodialysis. Haemodialysis involves the use of an extracorporeal system for removing toxins directly from the patient's blood by passing through a filtering unit, or dialyser. In conventional single-pass haemodialysis processes, patients are immobilised for the duration of the dialysis, which may take many hours. The therapy requires the provision of large volumes of purified (ultrapure) water for preparation of dialysate, which is used once and immediately discarded.

The other form of dialysis is peritoneal dialysis, which is commonly applied in Continuous Ambulatory Peritoneal Dialysis (CAPD) and Automated Peritoneal Dialysis (APD). In CAPD, fresh dialysate is infused into the patient's abdominal (peritoneal) cavity where, by means of diffusion, metabolic waste and electrolytes in the blood are exchanged with the dialysate across the peritoneal membrane. To allow sufficient diffusion of the electrolytes and metabolic wastes to occur, the dialysate is typically retained in the peritoneal cavity for a couple of hours before removal and replacement of the spent dialysate with fresh dialysate. Major drawbacks of CAPD include a low level of toxin clearance and the need to continuously replace the spent dialysate, which can be disruptive to the patient's daily activities. APD functions similarly to CAPD, except that it allows the dialysis to be performed at night or while the patient is resting, and allows the dialysate to be exchanged and replaced automatically.

Similarly to single-pass haemodialysis, both CAPD and APD require comparatively large volumes of dialysate, which limits the patient's freedom and mobility. There are devices that regenerate used dialysate from haemodialysis and/or peritoneal dialysis, as opposed to discarding it, to reduce the quantity of liquid used. The dialysate can be regenerated by passage through a sorbent that eliminates uremic toxins and excess electrolytes from the solution. For example, the original REDY (REcirculating DYalysis) Sorbent System includes a sorbent cartridge having five layers through which dialysis solution containing uremic waste metabolites flows in order to be regenerated.

A number of sorbent dialysis systems, such as the REDY, Allient or AWAK sorbent systems, employ a urease to convert urea, which (unlike other metabolic wastes such as creatinine and uric acid) is not readily adsorbed by activated carbon, into ammonium ions and bicarbonate ions. In the REDY system, a first layer consisting of activated carbon and hydrous zirconium oxide acts as a scavenger layer, and prevents inactivation of the urease by trace metal contaminants. The second layer contains urease adsorbed onto alumina particles. The third layer consists of buffered zirconium phosphate, which acts as a cation exchanger. As discussed in Drukker W. and van Doorn A. W. J. (1989) Dialysate Regeneration. In: Maher J. F. (eds) Replacement of Renal Function by Dialysis. Springer, Dordrecht, the zirconium phosphate is loaded with hydrogen ions and sodium ions in a ratio of 1:8. Ammonium ions, along with calcium, magnesium and potassium ions, are exchanged for hydrogen and sodium ions. The released hydrogen ions are partially buffered by the bicarbonate but there is a drop in pH due to release of hydrogen ions, a drop in carbonate concentration as a result of the buffering but, after an initial drop, a gradual increase in sodium ion concentration in the dialysate due to exchange of ammonium, calcium, magnesium and potassium ions for sodium ions. The fourth layer consists of hydrous zirconium oxide, which acts as an anion exchange resin and replaces phosphate in the dialysate with acetate. Finally, an activated carbon layer adsorbs creatinine, uric acid and other metabolites.

US patent publication no. 2010/0078387 discloses a sorbent cartridge comprising a combination of acid zirconium phosphate and alkaline hydrous zirconium oxide capable of restoring the balance of $Na^+$ and $HCO_3^-$ in spent dialysate to the levels found in fresh dialysate. In a preferred aspect the system relies on reducing pH and $Na^+$ in regenerated dialysate to a low level, and reducing $HCO_3^-$ to zero. A $NaHCO_3$ reinfusion system then brings pH, $Na^+$ and $HCO_3^-$ to desired levels.

PCT patent publication no. WO 02/43859 discloses a sorbent cartridge comprising layers of sodium zirconium carbonate and zirconium phosphate. The sodium zirconium carbonate layer adsorbs phosphate, while the zirconium phosphate adsorbs ammonia, $Ca^{2+}$, $Mg^{2+}$, $K^+$ and toxic heavy metals present in the spent dialysate fluids. The sorbent exchange profile is influenced by introducing a new compound, sodium zirconium carbonate, which acts to correct pH and release bicarbonate.

U.S. Pat. No. 6,818,196 discloses a method of making zirconium phosphate which involves treating sodium zirconium carbonate with caustic soda (sodium hydroxide) to form an alkaline hydrous zirconium oxide. This is subsequently heated and mixed with phosphoric acid to yield an acidic zirconium phosphate, which is further titrated with caustic soda to obtain the desired zirconium phosphate. The aim is to produce better quality zirconium phosphate for use in REDY sorbent cartridges.

U.S. Pat. No. 7,241,272 relates to the use of a resin bed in a cartridge for removing metabolic waste materials. It comprises at least four layers—a urease layer, a layer of zirconium phosphate, a layer of zirconium oxide and a layer of carbon. The zirconium phosphate layer, which contains two counter-ions $Na^+$ and $H^+$, can absorb $NH_4^+$, $Ca^{2+}$, $Mg^{2+}$ and $Na^+$. Release of the counter-ions is determined by the dialysate pH and the current loading state (pH) of the resin. The $Na^+$ ions are also released in exchange for $NH_4^+$, $Ca^{2+}$, $Mg^{2+}$ and K. Substantial fluctuations in pH, $Na^+$ and bicarbonate levels are apparent in most figures.

U.S. Pat. No. 8,580,112 describes a dialysis system which uses a sorbent cartridge comprising sodium zirconium carbonate, zirconium phosphate or other ammonia adsorbents, alumina, zirconium oxide, alumina supported urease, and granular activated carbon to remove waste materials. The dialysis system has a feedback control system which relies on conductivity sensing to measure sodium levels and controls the concentration of sodium ions in regenerated dialysate by adding water as diluent when required.

PCT publication no. WO 2009/157877 discloses a sorbent for removing metabolic waste products from a dialysis liquid. The sorbent comprises of a layer of immobilized uremic toxin-treating enzyme particles inter-mixed with cation exchange particles. However, there are still substantial pH, $Na^+$ and bicarbonate fluctuations, and the effect of calcium, magnesium and potassium ions is not discussed.

PCT publication no. WO 2005/123230 relates to a system that contains two sorbent-type cartridges in which one is for breaking down urea and releasing $Na^+$, while the other is for binding $Na^+$. The sorbent that decomposes urea and releases sodium comprises one or more layers of activated carbon, urease, zirconium phosphate and/or zirconium oxide. The sorbent that binds $Na^+$ can be a mixed bed ion exchange resin which comprises a cation exchange resin and an anionic exchange resin that are mixed and contained in the same housing. Dialysate sodium control is achieved by optionally including or bypassing the second sorbent. The system relies on feedback control by conductivity sensing to accurately control sodium.

PCT publication no. WO 2007/103411 discloses a dialysis system having a replaceable cartridge which uses cation rejecting membranes to reject Na, Ca, Mg and K while the remaining waste components diffuse across the membrane to contact a purification layer that removes heavy metals, oxidants and other uremic waste metabolites; a urea removal layer that eliminates urea from the solution but rejects cations; and an ion exchange layer that removes phosphate and sulfate. This presumably makes the purification system independent of Ca Mg and K concentration and presumably also prevents Na release in exchange for $NH_4$. Na profile is thus also expected to be independent of urea concentration.

US patent publication no. 2013/0213890 discloses a modular haemodialysis system with a sorbent cartridge that contains at least an activated carbon material for absorbing uremic waste and creatinine, and a zirconium oxide material to absorb phosphates from the dialysate. While enabling removal of urea, the cation exchange process releases sodium and hydrogen into the dialysate in a stoichiometric fashion. In order to maintain a stable composition of the dialysate, sodium ion concentration must be reduced either by absorption of sodium ions or by dilution. Further, the generation of carbon dioxide and hydrogen ions leads to pH instability of the dialysate that can require infusion of bicarbonate or other means to adjust pH.

US patent publication no. 2013/0199998 relates to a haemodialysis system having a controlled compliance dialysis circuit with a pump to control the flow of fluid between the dialysis circuit and the extracorporeal circuit across a dialysis membrane. The $Na^+$ concentration is monitored by measuring the conductivity of the dialysate and control is achieved by dilution.

There are problems associated with currently known methods. The $Na^+$ concentration in the dialysate initially falls but then gradually increases for the duration of the dialysis due to the exchange processes during dialysate regeneration. The gradual concentration change is then typically centred around a target concentration which is physiologically acceptable. For example, regenerated dialysate in the REDY system is typically characterised by sodium concentrations which increase from around 100 mEq/L to around 160 mEq/L over the period of the dialysis with an average of around 140 mEq/L. Therefore, while the $Na^+$ concentration might average the target concentration of 140 mEq/L when this approach is adopted, for most of the dialysis the $Na^+$ concentration is either above or below optimum.

Most commonly known sorbents, e.g. the REDY sorbent, are selected to deliver an approximately neutral overall sodium balance, and neutral pH conditions. This is done by pre-conditioning the sorbent materials such that both ammonium, as well as Ca, Mg and K are partially exchanged to protons, and partially exchanged to sodium (e.g. Drukker on REDY sorbent: H/Na loading ratio 1:8). There is an initial phase of low dialysate sodium concentration, followed by a gradual increase in dialysate sodium concentration and ending with a high final dialysate sodium concentration. Over the course of the entire therapy, the sodium concentration averages approximately at the desired physiological target sodium concentration. The sorbent and its exchange behaviour is designed to produce as neutral pH conditions as possible, while at the same time avoiding extreme low and extreme high sodium concentrations. In order to produce this exchange behaviour, the sorbent material is pre-conditioned and "pre-loaded" with sodium during synthesis. This is then often combined with a customised starting diaysate bath. The pre-loading may be applied to both, cation and anion exchangers. Further, some sorbents use chemical modifications of one of the ion exchange materials, such as e.g. the use of sodium zirconium carbonate as anion exchanger instead of hydrous zirconium oxide. All these modifications have in common that they are not directed at the differentiation of exchange behaviours between ammonium and other dialysate cations. They are merely directed at buffering pH fluctuations while at the same time preventing extreme sodium concentrations, without taking specific exchange selectivities into account.

Other known sorbents are selected to provide exchange properties which are more extreme, having either a very low sodium loading and providing approximately quantitative exchange of ammonium, Ca, Mg and K to protons, or having a very high sodium loading and providing approximately quantitative exchange of these cations for sodium. These systems require feedback-controlled infusion systems to correct the resulting extremely low or extremely high sodium concentrations in regenerated dialysate. This may be done by feedback-controlled mixing of the two types of regenerated dialysates (low Na and high Na), or by feedback-controlled infusion of $NaHCO_3$ (low-Na regenerated dialysate) or dilution with water (high Na regenerated dialysate).

None of these sorbents is selected for differential exchange behaviour for ammonium, and for Ca, Mg and K, respectively. All of these cations are generally assessed jointly, with the assumption of similar exchange ratio H/Na for all of these cations, which is jointly determined by the Na pre-loading of the sorbent during synthesis. In fact, the possibility of such differential exchange behaviour and its exploitation to produce a desired sodium exchange profile has previously not been recognised.

Rather, the ion exchange systems are pre-loaded with sodium in a way that produces the intended exchange profile (either equilibrated at a physiological equilibrium concentration, or brought to either extreme of complete exchange to proton, or sodium).

Other systems attempt to counter this gradual change with feedback systems, measuring the sodium concentration and then administering a concentrate solution or water to increase or decrease the final sodium concentration. Such feedback systems are complicated, costly, and prone to malfunctions. They typically rely on conductivity measurements which are known to be problematic and have limited accuracy. Further, they contribute to an increased physical size of the systems, and increased number of disposable components.

Existing sorbent systems are characterised by a substantial degree of sodium release in exchange for ammonium, potassium, calcium and magnesium. This leads to a steady addition of sodium to regenerated dialysate, which in turn results in a steady increase of the dialysate sodium concentration. Concurrently with sodium, other constituent concentrations, such as bicarbonate and chloride concentration, are also poorly controlled. This may result in undesirable and potentially harmful conditions for the patient, such as e.g. hyperchloremic acidosis. This is particularly relevant when chloride salts of Ca, Mg and K are used for reconstitution of spent dialysate. Some previous sorbent systems, such as e.g. the REDY system, used acetate salt solutions of Ca/Mg/K to counter or ameliorate such undesirable effects. However, these acetate salt solutions are known to be problematic for thermal sterilisation processes. Existing sorbent systems are therefore limited to use non-sterile solutions of these salts. Other salts of weak acids, such as bicarbonate or lactate salts have insufficient solubility to be of practical use for dialysate reconstitution.

The key problem with the above systems is that the selectivity of exchange behaviour between ammonium, and the other dialysate cations, Ca, Mg and K, has not been recognised, and hence the potential of exploiting such a selectivity in sorbent-based dialysate regeneration has not been recognised. The prior art goes to great lengths to strike a balance between low pH in regenerated dialysate and high sodium release. This is done by pre-loading the sorbents with Na during synthesis, providing barely acceptable pH profiles at the cost of significant sodium release. The patients are thus exposed to imperfect or potentially even harmful dialysate compositions for most of the dialysis.

SUMMARY

The present invention provides a sorbent for removing metabolic waste products from a dialysis liquid, the sorbent comprising a soluble source of sodium ions.

The soluble source of sodium ions may be present as a homogeneous mixture with at least one of: (a) uremic toxin-treating enzyme particles comprising a uremic toxin-treating enzyme immobilized on a solid support; (b) cation exchange particles configured to exchange ammonium ions for predominantly hydrogen ions and to exchange essential cations predominantly for sodium ions; and (c) anion exchange particles Accordingly, the present invention provides a sorbent for removing metabolic waste products from a dialysis liquid, the sorbent comprising a homogeneous mixture of: (a) uremic toxin-treating enzyme particles comprising a uremic toxin-treating enzyme immobilized on a solid support; (b) cation exchange particles configured to exchange ammonium ions for predominantly hydrogen ions and to exchange essential cations predominantly for sodium ions; and (c) anion exchange particles, and further comprising a soluble source of sodium ions.

Also provided is a process of preparing a sorbent comprising mixing a soluble source of sodium ions and at least one of: (a) uremic toxin-treating enzyme particles comprising a uremic toxin-treating enzyme immobilized on a solid support; (b) cation exchange particles configured to exchange ammonium ions for predominantly hydrogen ions and to exchange essential cations for sodium ions; (c) anion exchange particles; and (d) organic compounds absorber particles, and containing the mixture.

In a further aspect there is provided a sorbent which hydrolyses urea to ammonium and bicarbonate, and binds ammonium predominantly in exchange for protons. The protons exchanged for ammonium combine with bicarbonate, and the resulting carbonic acid is released as $CO_2$. The sorbent thus removes urea by conversion to $CO_2$. This produces repeatable chemical conditions in regenerated dialysate, which are independent of the spent dialysate urea concentration.

In a further aspect there is provided a sorbent which predominantly binds essential cations in exchange for sodium ions.

In a further aspect there is provided there is provided a sorbent which (a) hydrolyses urea to ammonium and bicarbonate, and (b) binds ammonium predominantly in exchange for protons and binds essential cations predominantly in exchange for sodium ions.

In a further aspect there is provided there is provided a sorbent cartridge comprising a sorbent as described herein housed in a cartridge.

In a further aspect there is provided there is provided a dialysis system for treating and recycling dialysate, the system comprising a sorbent cartridge as described herein which releases a predicted amount of sodium following ion exchange in the sorbent, a conduit for conveying spent dialysate from a source of spent dialysate to the sorbent cartridge, a conduit for conveying regenerated dialysate from the sorbent cartridge to the source of spent dialysate, and an infusate system for dosing an infusate solution comprising essential cations to the regenerated dialysate such that the solution combines with the predicted release of sodium ions from the sorbent cartridge to generate a predetermined dialysate sodium concentration.

The sorbent cartridge comprises a sorbent as described herein, which predominantly binds Ca, Mg and K in (stoichiometric) exchange for Na. The concentration of Ca, Mg and K in spent dialysate before sorbent regeneration is subject to only minor (absolute) fluctuations, and is largely controlled by the predetermined concentration generated through addition of infusate solution during the previous regeneration and reconstitution process. The essential cations are generally introduced in an infusate solution. The concentration of the essential cations in the infusate solution is chosen such that it matches the increase in Na released from prior exchange of Ca, Mg and K from spent dialysate on the sorbent. The combination of regenerated dialysate with this matching infusate solution results in the generation of a desired (predetermined) sodium concentration. Depending on the choice of infusate composition and infusion rate, the system can be adapted to produce specific sodium profiles, or maintain constant sodium concentration in regenerated dialysate without the need for a feedback control system.

Accordingly, in another aspect there is provided there is provided a process for regenerating dialysate in a dialysis process, comprising repeating the steps of:
(a) conveying spent dialysate from a source of spent dialysate to a sorbent which (a) hydrolyses urea to ammonium and bicarbonate, and (b) binds ammonium predominantly in exchange for protons and binds essential cations predominantly in exchange for sodium ions, to produce regenerated dialysate;
(b) introducing essential cations to the regenerated dialysate to reconstitute the dialysate; and
(c) conveying reconstituted dialysate from the sorbent to the source of spent dialysate;
characterised in that a predetermined concentration of sodium ions is generated following ion exchange in the sorbent.

In yet another aspect there is provided there is provided a kit comprising a sorbent as described herein and an infusate comprising salts of essential cations.

BRIEF DESCRIPTION OF THE DRAWINGS

In order that the disclosure may be readily understood and put into practical effect, reference will now be made to embodiments as illustrated with reference to the accompanying figures and the examples. The figures together with the description serve to further illustrate the embodiments of the invention and explain various principles and advantages.

DESCRIPTION

Figure 1:
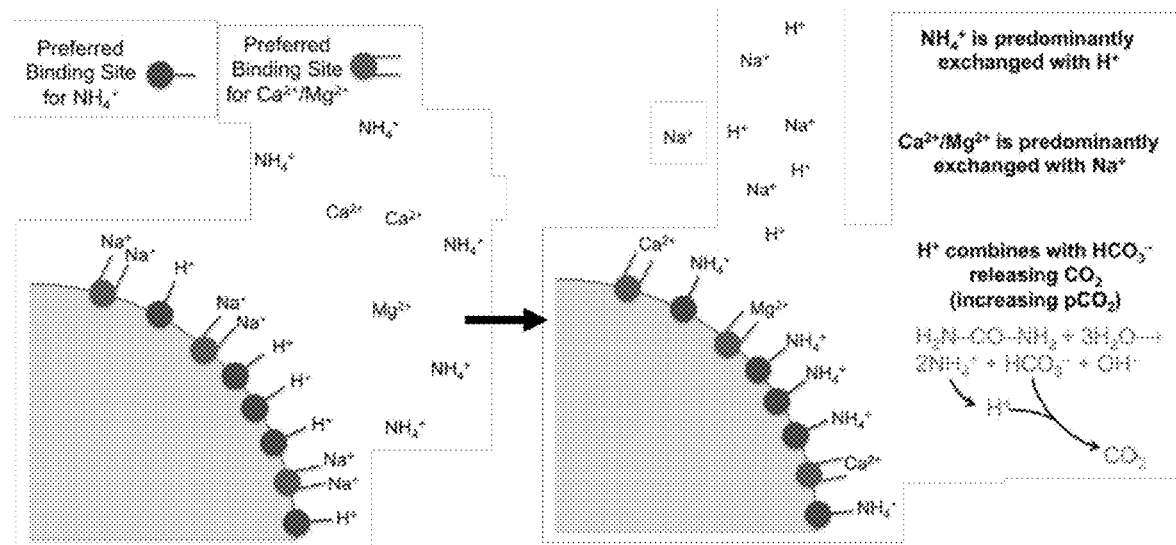
FIG. 1 is a schematic diagram showing a possible interpretation of the ion exchange characteristics of a cation exchanger in accordance with the current invention.

The present invention relates to a sorbent for removing metabolic waste products from a dialysis liquid. In particular the invention relates to a sorbent for removing metabolic waste products from a dialysis liquid, the sorbent comprising a soluble source of sodium ions. As described herein previous efforts to reduce the initial sodium drop in sorbent-based dialysis have been by modifying the sorbent during synthesis, or by infusion of salt solution to the regenerated dialysate. The sorbent comprises an ion exchange system which converts urea to ammonium ions, and which is configured to exchange ammonium ions for predominantly hydrogen ions and to exchange essential cations for predominantly sodium ions. This may comprise uremic toxin-treating enzyme particles, which may be intermixed with cation exchange particles as well as with anion exchange particles.

A combination of cation exchange material and anion exchange material is selected for properties, which favour ammonium to proton exchange, while essential cation to sodium exchange is unaffected. Therefore the sodium concentration in regenerated dialysate is independent of the ammonium (i.e. urea) concentration in spent dialysate. Rather, the absolute amount of sodium in regenerated dialysate is dependent on the sodium released in exchange for cations such as calcium, magnesium and potassium in spent dialysate, which are known to be subject to comparatively small (absolute) concentration fluctuations. In fact, the concentration of Ca, Mg and K is approximately equal to the concentration predetermined by the dialysate regeneration and reconstitution process in the dialysis system. The present invention thus also relates to using a sorbent as described above, in conjunction with an infusion (reconstitution) system configured to compensate the (approximately constant) sodium release originating from exchange of Ca, Mg and K during dialysate regeneration. The sorbent preferentially comprises a sufficient amount of soluble sodium salt to prevent an initial "sodium drop" in regenerated dialysate. Reconstitution, i.e. infusion of Ca, Mg and K ions is then done with a solution which is set to a concentration which matches the concentration of released sodium, thus resulting in a desired target sodium concentration after reconstitution. In practice, the infusate solution is provided at a total cation concentration which is approximately equal to the target sodium concentration.

Thus the present invention allows for a process for regenerating dialysate in which a predetermined amount of cations such as $Ca^{2+}$, $Mg^{2+}$ and $K^+$ is added to replenish dialysate from which metabolic waste products have been removed through contact with the sorbent as just described. The regenerated and reconstituted dialysate is reinfused to a patient in need of such treatment. Following dialysis, the spent dialysate will contain a known amount of the cations and will therefore release a corresponding amount of sodium ions from the sorbent; hence the sodium ion concentration is determined by the concentration of cations previously added to reconstitute regenerated dialysate. The result is an unprecedented exact control over the sodium concentration in regenerated and reconstituted dialysate, without the need for additional (feedback-controlled) re-infusion systems.

The above described ion exchange behaviour would previously not have been considered desirable, as it requires a comparatively low "pre-loading" of ion exchange material with sodium ions. Without the here described addition of a soluble sodium salt within the sorbent system, this would lead to a pronounced "sodium drop" in the early phase of sorbent-based dialysis treatment, with potentially harmful exposure of the patient to low concentrations of sodium, low pH and consequently low bicarbonate concentrations. Furthermore, without the addition of a soluble sodium salt, such an exchange system would likely result in a strongly negative total sodium balance, where excessive amounts of sodium would be removed from the patient in the early phase of a treatment, without being replenished in the later phase of the treatment.

To overcome these complications, the sorbent is combined with a soluble source of sodium ions, such as a soluble sodium salt, which may be intermixed with at least one component of the sorbent material. In contrast to previously described sorbents, this combination provides the unique advantages of differential exchange behaviour, while concurrently allowing the maintenance of physiological conditions necessary for a safe and effective dialysis treatment. The inclusion of a soluble sodium salt intermixed with sorbent materials also provides unique advantages over alternative approaches such as e.g. the use of a strongly basic anion exchange material intermixed with an acidic cation exchange material, or the use of sodium releasing anion exchange materials such as sodium zirconium carbonate, as these materials are characterised by partial exchange of ammonium to sodium, and thus increased release of sodium, and dependence of spent dialysate urea concentration, both contrasting with the here described sorbent properties of selective exchange behaviour for ammonium and Ca/Mg and K.

Furthermore, it would previously have been considered undesirable to provide a sorbent as described here, which is characterised by a regeneration process which continuously releases sodium, while entirely avoiding a phase of initial "sodium drop". In a conventional sorbent system, this situation would have been expected to lead to an excessive increase of dialysate sodium concentration, resulting in excessive release of sodium to the patient, and thus to a potentially harmful situation for the patient. This is efficiently prevented and controlled, by using a sorbent which exclusively releases sodium in exchange for Ca, Mg and K, by preventing a "sodium drop" through addition of a soluble sodium source, and by configuration of the reconstitution to use an infusate which has a concentration that matches the target dialysate sodium concentration.

The term "sorbent" as used herein broadly refers to a class of materials characterized by their ability to absorb the desired matter of interest.

The term "metabolic wastes" in the context of this specification, means any constituents, typically toxic constituents, within a dialysate that are produced by metabolism and which are desirable to be removed in a dialysate detoxification process. Typical metabolic wastes include, but are not limited to phosphates, urea, creatinine and uric acid.

The term "essential cations" as used herein refers to cations other than sodium ions that are present in dialysis solutions and are essential for their safe and effective use. These ions are generally calcium and magnesium ions but potassium ions may also be present. Calcium, magnesium and potassium are removed by the sorbent and need to be reintroduced to regenerated dialysate to reconstitute the dialysate.

The term "cation equivalents" or "total cation equivalents" refers to the sum of all positive charge equivalents, except protons in a solution. It is measured in mEq/L.

The term "sodium" or the symbol "Na" may be used in the specification to refer to sodium ions rather than to the element itself, as would be well understood by the person skilled in the art. Accordingly, the terms "sodium", "Na", "sodium ions" and "$Na^+$" are used interchangeably. Likewise, the terms "calcium", "magnesium" and "potassium" or the symbols "Ca", "Mg" and "K" may be used in the specification to refer to calcium ions, magnesium ions and potassium ions, respectively.

The term a "source of spent dialysate" as used herein is a reference to a source of dialysate however it is produced. The source may be any source of spent fluid where the regeneration of biological fluids takes place by exchange across a membrane. If, for example, the dialysis process is haemodialysis then the source of the spent dialysate will be a dialyser in a haemodialysis apparatus. In such apparatus streams of blood from a patient and dialysate are in counter-current flow, and exchange takes place across a membrane separating the streams. Alternatively it may be a patient as, for example, in peritoneal dialysis where dialysate is introduced to a patient's peritoneal cavity for exchange to take place.

The term "cation exchange particles" as used herein refers to particles capable of capturing or immobilizing cationic or positively charged species when contacted with such species, typically by passing a solution of the positively charged species over the surface of the particles.

The term "anion exchange particles" as used herein refers to particles capable of capturing or immobilizing anionic or negatively charged species when contacted with such species, typically by passing a solution of the negatively charged species over the surface of the particles.

The term "uremic toxin-treating enzyme" as used herein refers to an enzyme able to react with a uremic toxin as a substrate. For example, the uremic toxic-treating enzyme may be an enzyme able to react with urea as a substrate, with uric acid as a substrate, or with creatinine as a substrate. Uremic enzymes can be determined to have this function in vitro, for example, by allowing the enzyme to react with a uremic toxin in solution and measuring a decrease in the concentration of the uremic toxin. Examples of uremic toxin-treating enzymes include, but are not limited to, ureases (which react with urea), uricases (which react with uric acid), or creatininases (which react with creatinine).

The term "uremic toxin" as used herein refers to one or more compounds comprising waste products, for example, from the breakdown of proteins, nucleic acids, or the like, as would be well understood by the person skilled in the art. Non-limiting examples of uremic toxins include urea, uric acid, creatinine, and beta-2 ($\beta_2$) microglobulin. In healthy individuals, uremic toxins are usually excreted from the body through the urine. However, in certain individuals, uremic toxins are not removed from the body at a sufficiently fast rate, leading to uremic toxicity, i.e. a disease or condition characterized by elevated levels of at least one uremic toxin with respect to physiologically normal levels of the uremic toxin. Non-limiting examples of disorders associated with uremic toxins include renal disease or dysfunction, gout, and uremic toxicity in subjects receiving chemotherapy.

The term "uremic toxin-treating enzyme particles" as used herein refers to a uremic toxin-treating enzyme in particle form. The enzymes may be immobilized by way of a covalent or physical bond to a biocompatible solid support, or by cross-linking, or encapsulation, or any other means.

The term "soluble source" as used herein refers to a compound distinct from other components of the sorbent which may be added to and mixed with the other components, or be present as a separate layer or in a compartment separate from other sorbent components. It will usually be added to the sorbent in the form of solid particles which intermix with other solid particles in the sorbent.

The term "biocompatible" as used herein refers to the property of a material that does not cause adverse biological reactions to the human or animal body.

The term "homogeneous" as used herein refers to a substantially homogeneous mixture, meaning a mixture have the same proportions of the various components throughout a given sample, creating a consistent mixture. The composition of the mixture is substantially the same overall, although it will be appreciated that in mixing solid particles there may be regions in a sample where mixing is not complete.

The term "particle size" refers to the diameter or equivalent diameter of the particle. The term "average particle size" means that a major amount of the particles will be close to the specified particle size although there will be some particles above and some particles below the specified size. The peak in the distribution of particles will have a specified size. Thus, for example, if the average particle size is 50 microns, some particles which are larger and some particles which are smaller than 50 microns will exist.

The terms "regenerate" or "regenerated" as used herein refer to the action of detoxifying dialysate by destruction and/or absorption of uremic toxins by a sorbent.

The term "regenerated dialysate" as used herein refers to dialysate which has been detoxified by destruction and/or absorption of uremic toxins by a sorbent.

The term "reconstitute" or "reconstituted" as used herein refer to the action of converting regenerated dialysate to essentially the same state and chemical composition as fresh dialysate prior to dialysis.

The term "reconstituted dialysate" as used herein refers dialysate which has been converted to essentially the same state and chemical composition as fresh dialysate prior to dialysis.

The term "predominantly" as used herein is intended to represent a situation or state which occurs for the most part or principally, while not excluding the possibility that some amount of another situation or state also occurs to a minimal extent. For example, it may be >80% or >90% or >95% or greater than 99%. For the avoidance of doubt, the possibility that only that situation or state occurs, to the exclusion of all others, is covered by the term.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements. The terms may also be given an exclusive meaning equivalent to the term "consisting of" where the context requires this.

As used herein, the term "about", in the context of concentrations of components of the formulations, typically means±5% of the stated value, more typically+/−4% of the stated value, more typically±3% of the stated value, more typically,+/−2% of the stated value, even more typically±1% of the stated value, and even more typically+/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The uremic toxin-treating enzyme may be immobilized on any known support material, which can provide immobilization for the uremic toxin-treating enzyme particles. Immobilization may be by physical means such as by adsorption on alumina. In an embodiment non-immobilised enzyme is used. Alternatively, other methods are used to convert urea to ammonia.

In one embodiment, the support material is a biocompatible substrate to which the enzyme is covalently bound. The biocompatible material may be a carbohydrate-based polymer, an organic polymer, a polyamide, a polyester, or an inorganic polymeric material. The biocompatible substrate may be a homogeneous substrate made up of one material or a composite substrate made up of at least two materials. The biocompatible substrate may be at least one of cellulose, Eupergit, silicon dioxide (e.g. silica gel), zirconium phosphate, zirconium oxide, nylon, polycaprolactone and chitosan.

In one embodiment, the immobilization of the uremic toxin-treating enzyme on the biocompatible substrate is carried out by immobilization techniques selected from the group consisting of glutaric aldehyde activation, activation with epoxy groups, epichlorohydrin activation, bromoacetic acid activation, cyanogen bromide activation, thiol activation, and N-hydroxysuccinimide and diimide amide coupling. The immobilization techniques used may also involve the use of silane-based linkers such as (3-aminopropyl) triethoxysilane, (3-glycidyloxypropyl) trimethoxysilane or (3-mercaptopropyl) trimethoxysilane. The surface of the biocompatible substrate may be further functionalized with a reactive and/or stabilizing layer such as dextran or polyethyleneglycol, and with suitable linker- and stabilizer molecules such as ethylenediamine, 1,6-diaminohexane, thioglycerol, mercaptoethanol and trehalose. The uremic toxin-treating enzyme can be used in purified form, or in the form of crude extract such as extract of urease from Jack Bean or other suitable urease sources.

The uremic toxin-treating enzyme particles may be capable of converting urea to ammonium carbonate. In one embodiment the uremic toxin-treating enzyme is at least one of urease, uricase and creatininase. In a preferred embodiment, the uremic toxin-treating enzyme is urease.

In one embodiment, the uremic toxin-treating enzyme particles are urease particles.

In one embodiment the uremic toxin-treating enzyme particles have an average particle size in the range of from about 10 microns to about 1000 microns, about 100 microns to about 900 microns, about 200 microns to about 900 microns, about 300 microns to about 800 microns, about 400 microns to about 700, 500 microns to about 600 microns, about 25 microns to about 250 microns, about 25 microns to about 100 microns, about 250 microns to about 500 microns, about 250 microns to about 1000 microns, about 125 microns to about 200 microns, about 150 microns to about 200 microns, about 100 microns to about 175 microns, and about 100 microns to about 150 microns.

In one embodiment, 1000 to 10000 units of urease are immobilized on said biocompatible substrate. The overall weight of immobilized urease and the substrate ranges from about 0.5 g to about 30 g.

In one embodiment, the cation exchange particles comprise an amorphous, water-insoluble metal phosphate in protonated form. In one embodiment the metal is selected from the group consisting of titanium, zirconium, hafnium and combinations thereof. In one embodiment, the metal whose phosphate is poorly soluble in water is zirconium. Poorly soluble phosphates are to be understood here as phosphates having a solubility not higher than 10 mg/L in water. Preferably, the cation exchange particles are zirconium phosphate particles which are configured to exchange ammonium ions for predominantly hydrogen ions and to exchange essential cations for sodium ions.

In an embodiment the cation exchange particles are configured to exchange ammonium ions for predominantly hydrogen ions and to exchange essential cations for sodium ions by setting them to low pH during synthesis. To optimise this property, the cation exchange particles are typically set to low pH and low sodium loading during synthesis. In an embodiment the cation exchanger is synthesised in the presence of an acid. The pH is set by adjustment to a desired level, such as by titration with a base such as sodium hydroxide to raise the pH to a level which provides the desired differential exchange behaviour. The titration also serves to provide the cation exchange particles with a sufficient loading of sodium to enable the desired exchange of sodium for calcium, magnesium and potassium. In an embodiment the cation exchange material is zirconium phosphate. This may be synthesised in conventional processes such, for example, from Basic Zirconium Sulfate (BZS) or from zirconium carbonate by reaction with phosphoric acid. If other acids are used a source of the phosphate group must be provided. Typically the pH is set to be in the range of 3.5 to 5.0, advantageously about 4.5, by titration of the reaction product with a base.

The zirconium phosphate particles may have an average particle size in the range of from about 10 microns to about 1000 microns, about 100 microns to about 900 microns, about 200 microns to about 900 microns, about 300 microns to about 800 microns, about 400 microns to about 700, 500 microns to about 600 microns, about 25 microns to about 200 microns or from about 25 microns to about 150 microns or from about 25 microns to about 80 microns or from about 25 microns to about 50 microns or from about 50 microns to about 100 microns or from about 125 microns to about 200 microns, or from about 150 microns to about 200 microns, or from about 100 microns to about 175 microns, or from about 100 microns to about 150 microns or from about 150 microns to about 500 microns, or from about 250 microns to about 1000 microns. The zirconium phosphate particles may be immobilized on any known support material, which can provide immobilization for the zirconium phosphate particles. In one embodiment, the support material is a biocompatible substrate. In one embodiment, the immobilization of the zirconium phosphate particles is a physical compaction of the particles into a predetermined volume. In one embodiment, the immobilization of the zirconium phosphate particles is achieved by sintering zirconium phosphate, or a mixture of zirconium phosphate and a suitable ceramic material. The biocompatible substrate may be a homogeneous substrate made up of one material or a composite substrate made up of at least two materials Suitable cation exchange materials are materials which are configured to exchange ammonium ions for predominantly hydrogen ions and to exchange essential cations for sodium ions. This property may be determined by measuring the ion exchange capabilities of the material. Measuring the change in sodium ion concentration over time in the presence of calcium, magnesium and/or potassium ions ought to result in an increase in sodium ion concentration but there will be no change in the absence of calcium, magnesium and/or potassium ions even if ammonium ions generated by the breakdown of urea are present.

The anion exchange particles may comprise of an amorphous and partly hydrated, water-insoluble metal oxide in its hydroxide-, carbonate-, acetate-, and/or lactate-counter-ion form, wherein the metal may be selected from the group consisting of titanium, zirconium, hafnium and combinations thereof. In one embodiment, the metal is zirconium. The anion exchange particles may be zirconium oxide particles. Preferably, the anion exchange particles are hydrous zirconium oxide particles.

In an embodiment the anion exchange particles are set to an alkaline pH. In an embodiment they are set to a pH in the range of from 7 to 14. In an embodiment they are set to a pH of from 12 to 13. One way to achieve this is to saturate the anion exchange particles with a base. In an embodiment the base is selected from the group consisting of sodium hydroxide, sodium carbonate, sodium bicarbonate, potassium hydroxide, magnesium hydroxide; calcium hydroxide, calcium carbonate, magnesium carbonate, potassium carbonate, potassium bicarbonate, ammonium carbonate and ammonium hydroxide. Preferably the base is selected from the group consisting of sodium hydroxide, sodium carbonate and sodium bicarbonate. Alkaline anion exchange particles are preferred to produce the desired selective sorbent exchange properties for ammonium and Ca/Mg/K, respectively, particularly when combined with acidic cation exchange particles as described above. It will be appreciated that the metal oxides used as anion exchange materials are typically synthesised by converting a precursor such as a carbonate to the oxide by reaction with hydroxide, followed by an optional titration, and that not washing the product will retain excess hydroxide within the product. If a sodium salt is used then the base can act as the source of sodium ions, hence sodium hydroxide is preferred if unwashed anion exchange particles are used.

The zirconium oxide particles may have an average particle size in the range of from about 10 microns to about 1000 microns, about 100 microns to about 900 microns, about 200 microns to about 900 microns, about 300 microns to about 800 microns, about 400 microns to about 700, 500 microns to about 600 microns, about 10 microns to about 200 microns or from about 10 microns to about 100 microns or from about 10 microns to about 30 microns or from about 10 microns to about 20 microns or from about 20 microns to about 50 microns or from about 25 microns to about 50 microns or from about 30 microns to about 50 microns or from about 40 microns to about 150 microns or from about 80 microns to about 120 microns or from about 160 microns to about 180 or from about 25 microns to about 250 or from about 250 microns to about 500 or from about 250 microns to about 1000. The zirconium oxide particles may be immobilized on any known support material which can provide immobilization for the zirconium oxide particles. In one embodiment, the immobilization of the zirconium phosphate particles is a physical compaction of the particles into a predetermined volume. In one embodiment, the immobilization of the zirconium oxide particles is achieved by sintering zirconium oxide, or a mixture of zirconium oxide and a suitable ceramic material. In one embodiment, the support material is a biocompatible substrate. The biocompatible material may be a carbohydrate-based polymer, an organic polymer, a polyamide, a polyester, a polyacrylate, a polyether, a polyolefin or an inorganic polymeric or ceramic material. The biocompatible substrate may be at least one of cellulose, Eupergit, silicon dioxide, nylon, polycaprolactone and chitosan.

In one embodiment, the zirconium oxide particles may be replaced by any particles that are able to absorb phosphate ions and other anions. Preferably, the particles are able to absorb anions selected from the group comprising ions of phosphate, fluoride, nitrate and sulphate. The zirconium oxide particles may also release ions such as acetate, lactate, bicarbonate and hydroxide in exchange for the anions absorbed. In one embodiment, the zirconium oxide particles are also good binders for iron, aluminium and heavy metals selected from the group consisting of arsenic, bismuth, cadmium, cobalt, copper, lead, mercury, nickel, palladium and silver.

In an embodiment the ratio of cation exchange particle to anion exchange particle is in the range of 1:1 to 5:1. In an embodiment the ratio of cation exchange particle to anion exchange particle is in the range of 2:1 to 3:1. In an embodiment the ratio of cation exchange particle to anion exchange particle is about 2.4:1. The anion exchanger acts as a pH buffer for the low pH cation exchanger however, at this ratio, the buffer capacity of anion exchanger particles alone is insufficient to compensate for the acidification and the drop in sodium concentration by the cation exchanger.

The sorbent comprises a soluble source of sodium. The provision of sodium overcomes the initial drop in sodium concentration. Accordingly a sorbent material in accordance with the present invention will exhibit a lesser drop in sodium ion concentration compared to conventional materials in an initial phase of a dialysis process. Ideally there will be no initial drop in sodium ion concentration.

In an embodiment the soluble source of sodium ions may be particles of a soluble salt. In an embodiment the soluble salt is a basic salt. In an embodiment the soluble salt is selected from one or more of the group consisting of sodium carbonate, sodium bicarbonate and sodium hydroxide. It may also be a neutral salt, such as sodium chloride, or a salt of a weak acid such as e.g. sodium lactate or sodium acetate.

The production of the desired exchange selectivity requires a comparatively low Na-loading of the sorbent materials during synthesis. Therefore it is necessary to add a separate source of sodium ions to overcome the initial Na-drop caused by the sorbent material.

The sorbent comprises bicarbonate which is both generated in the breakdown of urea and carried from the patient in the dialysate. There is an initial drop in bicarbonate concentration due to neutralisation with hydrogen ions released from the cation exchanger, which results in formation of carbon dioxide. Carbonate and/or bicarbonate may be introduced by adding a salt directly to the sorbent to compensate. This could be done by introducing, for example, sodium carbonate, sodium bicarbonate, or by introducing weak acid salts such as sodium acetate or sodium lactate which result in an increased bicarbonate in the dialysate. The sodium salt is preferred since it may also act as a source of sodium. There also needs to be a pH balance achieved since the amount of anion exchanger is insufficient to compensate for the low pH cation exchanger. The balance may be achieved by the introduction of a basic material such as e.g. sodium hydroxide, sodium carbonate or sodium bicarbonate While such compounds could be added separately to address each of the drops, it will be appreciated that the introduction of sodium carbonate or sodium bicarbonate addresses all deficiencies; hence sodium carbonate and sodium bicarbonate are the preferred source of sodium ions.

While not wishing to be bound by theory, it is believed that the sorbent predominantly converts urea to $CO_2$, allowing for the chemistry of sorbent-based dialysate regeneration to be largely independent of the urea concentration in the spent dialysate. In a first step, urea contained in spent dialysate is converted to ammonium and bicarbonate. In a second step, the ion exchanger exchanges ammonium predominantly with protons. The protons then recombine with bicarbonate to form $CO_2$, which is released from the system. Cations such as calcium, magnesium and potassium are predominantly exchanged with sodium. Advantageously the sorbent is a homogeneous mixture containing a calculated amount of sodium carbonate and/or sodium bicarbonate. The addition of sodium carbonate/sodium bicarbonate influences the sodium concentration in regenerated dialysate, without changing the sorbent's exchange characteristics.

The sorbent may optionally contain carbonic anhydrase to facilitate the $CO_2$ release. Carbonic anhydrase catalyses a reaction in which carbon dioxide and water are converted to carbonic acid, protons and bicarbonate ions. By way of example, carbonic anhydrase from human or bovine erythrocytes and recombinant human carbonic anhydrase may be used. Carbonic anhydrase may be immobilized on any known support material, as described previously for the uremic toxin-treating enzyme particles. Carbonic anhydrase may be immobilized separately to the uremic toxin-treating enzyme particles or to the same particles. In one embodiment the sorbent further comprises an organic compounds absorber. The organic compounds absorber may be intermixed with the uremic toxin-treating enzyme particles and cation exchange particles and/or anion exchange particles, or may form a separate layer. The organic compounds absorber may be selected from the group consisting, amongst others, of activated carbons, molecular sieves, zeolites and diatomaceous earth. The organic compounds absorber particles may be activated carbon particles. In one embodiment, the organic compound absorber in the primary layer is an activated carbon filter pad. In another embodiment, the organic compound absorber comprises activated carbon particles.

The activated carbon particles may have an average particle size in the range of from about 10 microns to about 1000 microns, about 10 microns to about 250 microns, about 20 microns to about 200 microns, about 25 microns to about 150 microns, about 50 microns to about 100 microns, about 25 microns to about 250 microns or from about 100 microns to about 200 microns or from about 100 microns to about 150 microns or from about 150 microns to about 300 microns or from about 200 microns to about 300 microns or from about 400 microns to about 900 microns or from about 500 microns to about 800 microns or from about 600 microns to about 700 microns or from about 250 microns to about 500 microns or from about 250 microns to about 1000 microns.

In one embodiment, the activated carbon particles may be replaced by any particles that are able to absorb organic compounds. Preferably, the particles are able to absorb organic compounds and/or organic metabolites selected from the group comprising creatinine, uric acid and other small and medium sized organic molecules without releasing anything in exchange. The activated carbon particles may also be physically compacted into a predetermined volume for the purpose of space economy. In one embodiment, the activated carbon particles are physically compacted into an activated carbon filter pad.

The invention also provides a process of preparing a sorbent comprising mixing immobilized uremic toxin-treating enzyme particles which convert urea to ammonium ions with cation exchange particles, configured to exchange ammonium ions for predominantly hydrogen ions and to exchange essential cations for sodium ions, and further comprising providing a sodium source, and optionally mixing anion exchange particles and/or organic compounds absorber particles.

In one embodiment, the sorbent is housed in at least one cartridge. The sorbent cartridges may be configured such that they are easily removable from the dialysis device. The sorbent cartridge may also be compact and made of a material that is resistant to wear and tear. The cartridge may be made from resilient, chemically and biologically inert materials. The cartridge may also be able to withstand the pressure within the flow system of the dialysis device without leakage. The cartridge may be made from material which can withstand sterilization conditions such as heat sterilization, ethylene oxide sterilization and sterilization with ionizing radiation. In one embodiment, the sorbent cartridges are made of acrylonitrile butadiene styrene. The sorbent cartridges may also be made of polycarbonate, polypropylene or polyethylene. In one embodiment, filter pads and filter papers may also be located at the in- and outlet of the sorbent cartridges and/or between the individual layers within the sorbent, to filter off any particles arising from the layers of the sorbent.

The invention also relates to a process for regenerating dialysate in which a predetermined amount of cations such as $Ca^{2+}$, $Mg^{2+}$ and $K^+$ is added to replenish dialysate from which metabolic waste products have been removed through contact with the sorbent of the present invention. Following dialysis, the spent dialysate will contain a known amount of the cations and will therefore release a corresponding amount of sodium ions from the sorbent; hence the sodium ion concentration in regenerated dialysate is determined by the amount of cations previously added to reconstitute the dialysate. The system uses a sorbent, which predominantly converts urea to $CO_2$, and predominantly exchanges cations such as calcium, magnesium and potassium to sodium. The concentration of the infusate is chosen such that the amount of sodium exchanged for the constituents of the infusate (Ca, Mg, K) results in a desired target sodium concentration, when recombined with the infusate volume used for reconstitution with Ca, Mg and K. Thus the system for dialysate regeneration and reconstitution comprises an intrinsically regulated infusion system. The system can produce specific sodium profiles, or maintain constant sodium concentration in regenerated dialysate without the need for a feedback control system.

One advantages of this invention is the ability to maintain sodium levels in the dialysis solution within a desired range. This can help to reduce discomfort experienced by the patient as a result of increased or decreased sodium levels in the patient's blood.

The system of this invention is able to control the dialysate sodium concentration with significantly smaller variations than conventional dialysis apparatus. For example, accuracies of ±5% of a target concentration are achievable. For example the system can maintain dialysate sodium concentrations within a range from 132 to 145 mEq/L. Further, specific concentration profiles are accessible, e.g. for "sodium modelling", and can equally be achieved with ±5% accuracy. Bicarbonate and chloride concentrations are significantly better controlled than in prior art.

The sorbent system of this invention allows the use of chloride salts for electrolyte re-infusion, whereas previous systems had to use salts of a weak acid, such as acetate salts in order to keep dialysate buffer system (buffer concentration and Cl concentration) within physiological range. Acetate salts are more costly, and more troublesome to be provided in a sterile and stable form (changes of composition during sterilisation and storage) than chloride salts. However, while the present invention allows the possibility to provide infusate solutions based on chloride salts of Ca, Mg and K, the system is not limited to these salts. Chloride salts may partially be replaced by lactate salts, without changing the total salt concentration or the infusion ratio. As there would only be a partial replacement of chloride by lactate, the resulting infusate solution would not be limited by solubility issues. Advantageously, such mixed salt solutions may be used to increase the buffer capacity of a regenerated dialysate, countering a patient's acidosis. More advantageously, such solutions may be similar to commercially available solutions for parenteral infusion, and may be suitable for steam sterilisation.

The resulting system is simple, robust, small, cost efficient, and has a smaller number of components as compared to prior art. While not wishing to be bound by theory, it is believed that this is due to the characteristic of the sorbent to exchange ammonium predominantly to protons, while bivalent cations and potassium are predominantly exchanged to sodium. This is a result of the sorbent ion exchange design (zirconium phosphate), which is deliberately set to lower pH and lower sodium loading during sorbent synthesis. Surprisingly, it was found that the cation exchange properties for calcium, magnesium and potassium are independent of the sorbent pH, while the ammonium exchange property is strongly dependent on the pH. This allows one to produce an ion exchange material with a pH that favours ammonium to proton exchange, while for calcium, magnesium and potassium to sodium exchange is unaffected. The sorbent of the current invention combines such optimized zirconium phosphate with alkaline pH hydrous zirconium oxide in order to maintain the pH of regenerated dialysate within a desired target range, e.g. from 6.0 to 8.0, while not interfering with ion exchange selectivity. This system is subject to a marked Na-drop to a dialysate Na-concentration of approx. 100 mEq/L in the early phase of dialysis. To counter this Na-drop, a calculated amount of sodium bicarbonate, sodium carbonate, sodium chloride or sodium hydroxide is added to the homogeneous sorbent mixture.

In consequence, the sodium concentration in regenerated dialysate is independent of the ammonium (i.e. urea) concentration in spent dialysate. Rather, the absolute amount of sodium exchange is dependent on the concentrations of calcium, magnesium and potassium in spent dialysate, which are known and subject to only minor fluctuations. These concentrations are in fact determined by the dialysate regeneration and reconstitution process in the dialysis system. For example, typical K, Ca and Mg concentrations are 2, 3 and 1 mEq/L. That is, the actual amount of sodium released during the regeneration process is known, and is directly dependent of the K, Ca, and Mg concentrations determined by the system during the regeneration process. This allows calculation of the concentration of the solution used to administer K, Ca and Mg such that the volume increase through infusion of this concentrate accurately matches the sodium increase caused by the ion exchange of K, Ca, and Mg. For example, the concentration of the K, Ca, and Mg solution can be set such that the equivalents of sodium released in return for the combined equivalents of K, Ca and Mg are met by the required volume of solution to produce a desired target Na concentration of e.g. 138 mEq/L. For example, the regeneration of 1 L of spent dialysate containing 3 mEq/L of K, 3 mEq/L of Ca and 1 mEq/L of Mg may result in a total release of 5 to 7 mEq, e.g. 7 mEq of sodium. The system of the current invention advantageously administers a concentrate solution to reconstitute K, Ca and Mg, which has a total volume of 51 mL to reconstitute said 1 L of spent dialysate. 7 mEq of sodium increase thus meet with 51 mL of volume increase, which results formally in a sodium concentration of 7/0.051 mEq/L=138 mEq/L in the added fluid components. Crucially, this concentration is the same as the target concentration and thus does not affect the sodium concentration in the total regenerated volume of 1.051 L. Based on this model, the preferred mixing ratio of regenerated dialysate and K, Ca and Mg concentrate is 1000:51. It should be noted that this mixing ratio is based on an idealised calculation, which may be further fine-tuned by empirical optimisation. In practice the concentration of sodium ions and the essential ions is prescribed by a physician. Several configurations can be provided, which may differ by composition of the infusate solution, or by the dose volume of infusate solution. A steady state with regard to sodium concentration may be maintained. Alternatively, other mixing ratios can produce an intentional deviation from a target concentration, e.g. as in sodium modelling. Alternatively, different target concentrations of Ca, Mg, K and Na may be achieved using different concentration solutions and different infusion volume ratios.

In an embodiment the infusate concentrate solutions may further comprise osmotic agents such as glucose, to ensure correct osmotic pressure of dialysate after infusion.

In an embodiment the infusate concentrate solutions may further comprise additional salts such as sodium chloride, which can function as a variable component, or "placeholder" substituting other chloride salts for different target concentrations of Ca, Mg and K. Advantageously, this allows the provision of a series of infusate concentrates which can all be administered using the same infusion volume ratio, thereby facilitating device design. For example, such concentrate solutions may also contain an intentionally low sodium chloride concentration, thus allowing the creation of a negative sodium gradient in dialysate after infusion.

Non-limiting examples which embody certain aspects of the invention will now be described.

DETAILED DESCRIPTION OF DRAWINGS

Two experimental setups of different scales were used. The differences were as shown in Table 1.

TABLE 1

|  | Miniature Size | Full Size |
|---|---|---|
| Total Volume | Dialysate + simulated patient blood 300 mL Infusate 30-140 mL | Dialysate 2 L Infusate 4-5 L Simulated patient 40 L |
| Dialysate flow rate | 9.1 mL/min | 300 mL/min |
| Infusate flow rate | 0.126-0.583 mL/min | 15-20 mL/min |
| Total therapy volume | 2.18 L | 72 L |
| Time | 4 h | 4 h |
| Total urea challenge | 19 mmol | 640 mmol (18 g urea-N) |
| Total salt infusion | 15 mEq | 500 mEq |

Components of Infusion/Toxin Solution:
Cations infusate: $Ca^{2+}$— 1.5 mmol/L, $Mg^{2+}$— 0.5 mmol/L, $K^+$— 3.0 mmol/L; and
Toxin: urea—8.9 mmol/L, creatinine—370 μmol/L and phosphate—1.3 mmol/L.

Figure 2:
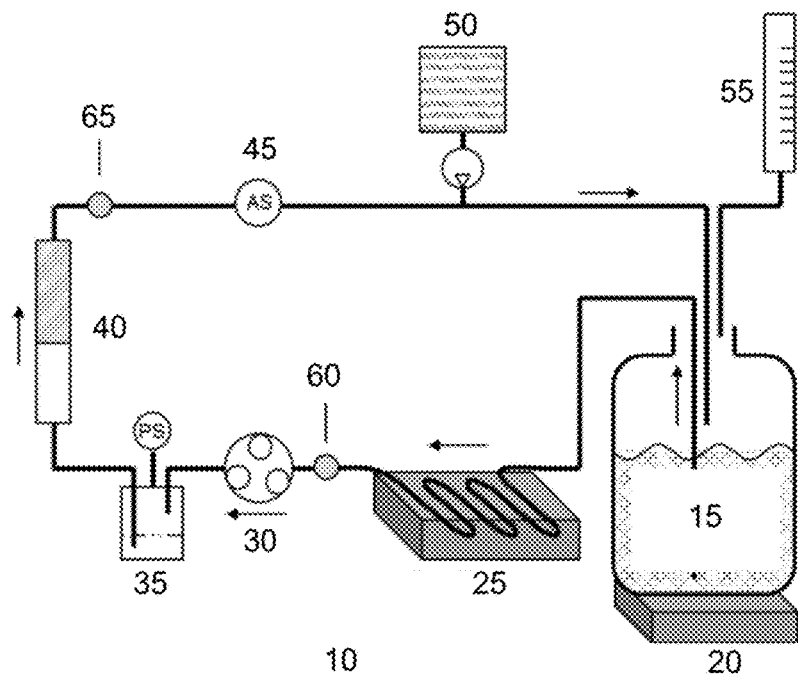
FIG. 2 is a schematic diagram illustrating a single loop dialysis system for testing sorbents.

In conventional sorbent dialysis arrangements, 6 L of dialysate and up to 1 L of infusate are used. In an embodiment of the present invention, 2 L of dialysate and 4 to 5 L of infusate are used. Accordingly, the total fluid volume required to complete the dialysis therapy is relatively unchanged in the present invention as compared to conventional sorbent dialysis. Conventional sorbent dialysis uses a large dialysate reservoir volume (as large as 6 L for a REDY system) to buffer changes in sodium, bicarbonate, and pH; while infusate was kept to a smaller volume (1 L). In the current invention, although a larger infusate volume is used to achieve the required infusion, the dialysate reservoir is no longer required to act as a buffer volume and can be reduced to 2 L:

The miniature setup 10 is as shown in FIG. 2. The process first involves drawing a sample flow from a spent dialysate reservoir 15 fitted with a stirrer 20, in which the dialysate flow is heated at 37° C. by a heat exchanger 25. The flow rate is controlled by a pump 30, coupled to a pressure dampener and sensor 35. Initially, a solution containing urea is introduced to the spent dialysate reservoir. This mimics spent dialysate from a first cycle of dialysis once it is heated by passage through the heat exchanger 25. The spent dialysate then passes through a sorbent cartridge 40 to produce a regenerated dialysate. The level of ammonia may be monitored by an ammonia sensor 45. One suitable ammonia sensor is disclosed in WO2017/034481, the contents of which are incorporated herein by reference. An infusate/toxin solution 50 is fed into the regenerated dialysate in this experimental system. The purpose is both to maintain the salt concentration as described herein and to closely mimic the conditions when patients are treated. The experimental system adds toxins together with the infusate but it will be appreciated that the infusate would ordinarily be introduced to the regenerated dialysate before the dialysate is reused for dialysis. In peritoneal dialysis the reconstituted dialysate would be introduced to the peritoneal cavity of the patient for diffusion of toxins to take place, while in haemodialysis toxins diffuse across a membrane as reconstituted dialysate flows through a dialyser in the opposite direction to the patient's blood. In the experimental system the reconstituted dialysate contains toxins and so is treated as spent dialysate for a second cycle. The spent dialysate is returned to the spent dialysate reservoir 15. The spent dialysate is drawn from the spent dialysate reservoir for treatment in the sorbent in a second cycle. A gas burette 55 measures the volume of carbon dioxide gas that is produced in each cycle. A sample of the spent dialysate and regenerated dialysate was collected through sample ports 60 (spent dialysate) and 65 (regenerated dialysate), respectively, in each cycle for analysis. The miniature setup 10 was used in investigating the effect of how different components of the dialysate affect the release of $Na^+$ over time.

The sorbent in the sorbent cartridge 40 varies depending upon the experiment. In each case it includes immobilized uremic toxin-treating enzyme particles which convert urea to ammonium ions, intermixed with cation exchange particles. The cation exchange particles are configured to exchange ammonium ions for predominantly hydrogen ions and to exchange calcium, magnesium and potassium ions for sodium ions in the current invention. The cation exchange material operates at a pH that favours ammonium to proton exchange, while bivalent cation to sodium exchange is unaffected (FIG. 1). Therefore the sodium concentration in regenerated dialysate is independent of the ammonium (i.e. urea) concentration in spent dialysate.

The toxin/infusate solution 50 consisted of an aqueous solution of Ca, Mg, K salts as well as urea, creatinine and a source of phosphate. Ca, Mg, and K were typically introduced as chloride salts. In this experimental system, phosphate was introduced to mimic normal waste generation. Typically the phosphate was introduced as $H_3PO_4$ or $KH_2PO_4$. Where $KH_2PO_4$ was used a source of phosphate, the mass of KCl was correspondingly reduced in a 1:1 molar ratio in order to achieve the same target concentration of K.

Figure 3:
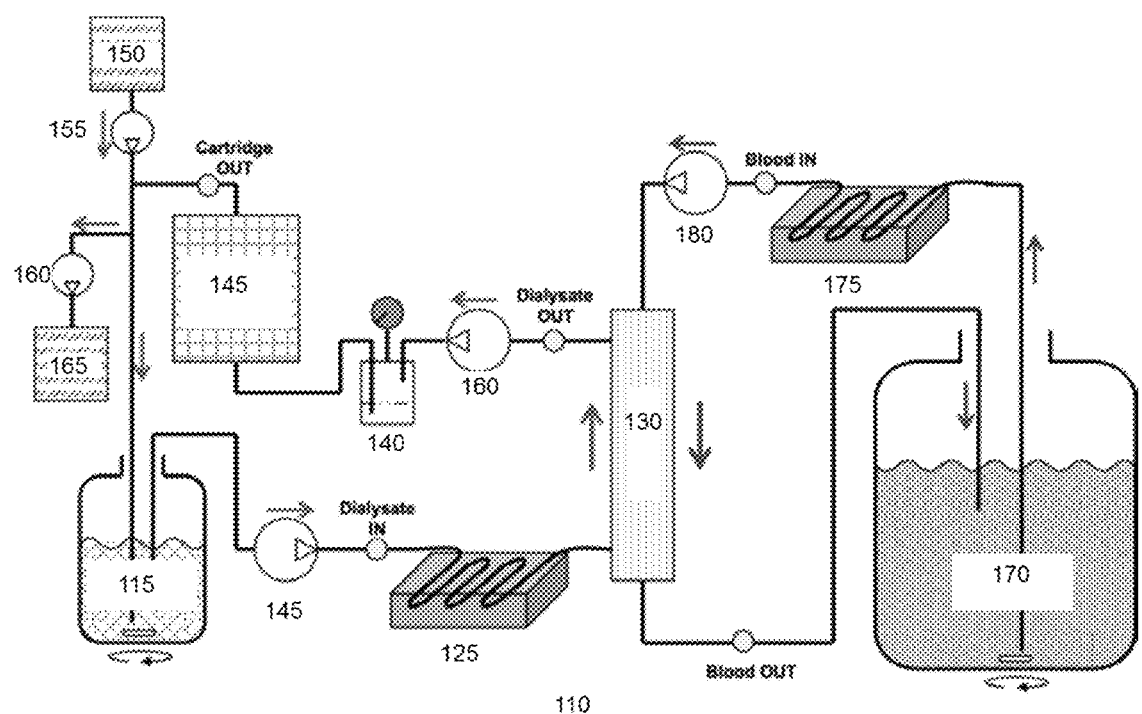
FIG. 3 is a schematic diagram illustrating a double loop dialysis system for testing sorbents.

The full scale setup 110 is as shown in FIG. 3. The double-loop process resembles that of the miniature setup but further includes a second circuit for a simulated patient's blood. An aqueous dialysate solution is used to simulate patient's blood. The process first involves pumping a sample flow from a dialysate reservoir 115 via a pump 145, through a heat exchanger 125 at 37° C. to dialyser 130 where exchange with simulated blood takes place. The simulated blood was pumped out from a reservoir 170 via a pump 180, through a heat exchanger 180 at 37° C. The heated simulated blood then passed through the dialyser 130 before returning to the patient reservoir 170. Simulated blood and dialysate flow to either side of a membrane (not shown) across which they exchange. The spent dialysate is then pumped out of the dialyser 130 via a pump 135 and into a pressure dampener gauge 140, before it is passed through a sorbent cartridge 145 to regenerate the dialysate. An infusate solution 150, controlled by an infusion pump 155, is fed into the regenerated dialysate to reconstitute the dialysate. Excess fluid is optionally removed by a drain pump 160 into a drain reservoir 165, while the remaining regenerated dialysate is fed into the dialysate reservoir 115.

Non-limiting examples which embody certain aspects of the invention will now be described.

EXAMPLES

Example 1—Preparation of Zirconium Phosphate

Zirconium phosphate is synthesised by conventional methods, for example by reaction of an aqueous mixture of Basic Zirconium Sulfate and phosphoric acid as described in U.S. Pat. No. 3,850,835. Alternatively, it is synthesised from an aqueous mixture of Sodium Zirconium Carbonate and phosphoric acid as described in U.S. Pat. No. 4,256,718.

The product was titrated to a solution pH of 4.5. A 5M solution of sodium hydroxide was added step-wise to an aqueous slurry of the zirconium phosphate until a pH of 4.5 was reached. After the titration, the zirconium phosphate was washed until the filtrate was within acceptable limits of leachables, and air dried.

Example 2—Preparation of Hydrous Zirconium Oxide

Hydrous zirconium oxide is synthesised by conventional methods, for example by reaction of an aqueous mixture of sodium zirconium carbonate and sodium hydroxide as described in U.S. Pat. No. 4,256,718. After synthesis of hydrous zirconium oxide, the product was titrated to a pH of from 12 to 13. This was done by making an aqueous slurry of the hydrous zirconium oxide and titrating it with 5M sodium hydroxide until the slurry is at a pH of 12 to 13. In some instances, the hydrous zirconium oxide was then washed until the concentration of leachables in the filtrate was within acceptable levels, and air dried. Alternatively, the HZO was recovered directly from the slurry and not washed before being air dried. The HZO subjected to a washing procedure is referred to as "washed HZO". The HZO recovered directly from the titration slurry is referred to as "unwashed HZO".

Example 3—Preparation of Sorbent Mixture for Miniature Cartridges

For each experiment, the sorbent cartridge consisted of the materials listed below. Zirconium phosphate (ZP) was prepared according to example 1. Hydrous zirconium oxide (HZO) was prepared as described in example 2, and both washed an unwashed material were used as indicated. Immobilised urease (IU) was prepared as described in examples 1 and 2 of WO 2011/102807, the contents of which are incorporated herein by reference. Activated carbon (AC) has a particle size of 50 to 200 micron. In general, one experimental condition was changed at a time in order to distinguish the effect of that modification on the sodium concentration of the regenerated dialysate. The sodium and pH set point of the sorbent was adjusted in two ways in these experiments:

1) Use of soluble additive ($Na_2CO_3$, $NaHCO_3$), and/or
2) Modification of HZO—use of un-washed and washed HZO In each experiment, a glass flex-column with inlet and outlet was used as receptacle for the sorbent. The sorbent materials, immobilised urease and additive were weighed individually, then mixed together and dry packed into the flex-column. The sorbent bed was secured in place with a plug of cotton wool, at which point it was ready for installation into the dialysate circuit.

Figure 9:
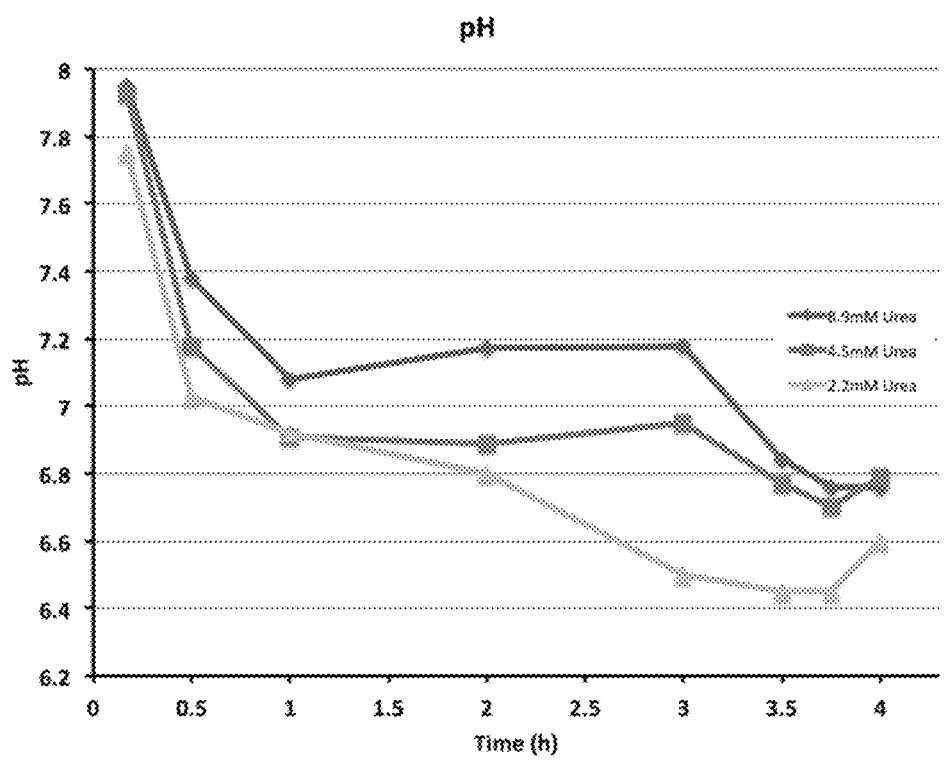
FIG. 9 is a graph showing the effect of patient urea level on pH.

Miniature Cartridge Experiments d) pH: pH profile shows only a weak dependency on dialysate urea concentration (FIG. 9). Acidification through formal loss of $HCO_3^-$ and an increase of $Cl^-$ from infusate addition is seen.

TABLE 2

| | Example title | | | | | | | | | |
|---|---|---|---|---|---|---|---|---|---|---|
| | Effect of urea concentration on dialysate chemistry | | | Effect of Ca, Mg, K infusion on dialysate chemistry | | Improved Na profile after modification of sorbent | | Control of Na profile by modification of sorbent and infusate composition | | |
| Example | 4 | | | 5 | | 6 | | 7 | | |
| FIG. | 4a, 6, 7, 8, 9 | | | 4b, 10, 11, 12 | | 13, 14, 15 | | 6a, 6b, 6c | | |
| Urea level | 2.23 mM | 4.47 mM | 8.93 mM | 0.00 mM | 8.93 mM | 8.93 mM | 8.93 mM | 8.93 mM | 8.93 mM | 8.93 mM |
| Ca, Mg, K | Yes | Yes | Yes | Yes | No | Yes | Yes | Yes | Yes | Yes |
| ZP (g) | 40 | 40 | 40 | 40 | 40 | 40 | 40 | 40 | 40 | 40 |
| HZO - washed (g) | 17 | 17 | 17 | 17 | 17 | 17 | 17 | 17 | 17 | 17 |
| AC (g) | 8.8 | 8.8 | 8.8 | 8.8 | 8.8 | 8.8 | 8.8 | 8.8 | 8.8 | 8.8 |
| IU (g) | 1.0 | 1.0 | 1.0 | 1.0 | 1.0 | 1.0 | 1.0 | 1.0 | 1.0 | 1.0 |
| $Na_2CO_3$ (g) | 0.54 | 0.54 | 0.54 | 0.54 | 0.54 | — | — | 0.54 | 2.2 | 2.2 |
| $NaHCO_3$ (g) | — | — | — | — | — | 0.43 | 0.86 | — | — | — |
| Infusate vol (mL) | 30 | 30 | 30 | 30 | 30 | 30 | 30 | 30 | 30 | 141 |

Example 4—Effect of Urea Concentration on Dialysate Chemistry

Three identical sorbent cartridges were constructed using a composition as given in Table 2 and tested in the recirculating miniature dialysis setup 10 described above. The three cartridges were challenged with either low, medium or high urea concentrations in the recirculating miniature dialysis setup 10 described above with reference to FIG. 2, representing a range of incoming patient urea levels. Briefly, dialysate solutions containing low, medium and high concentrations of urea (2.2 mM, 4.5 mM and 8.9 mM) were prepared for use as the initial dialysate solution. The toxin/infusate solution 50 was prepared so as to contain sufficient urea to maintain either the low, medium or high urea level as well as the required $Ca^{2+}$, $Mg^{2+}$, $K^+$, creatinine and phosphate concentrations. In each of the three experiments, toxin-containing dialysate was pumped through the sorbent cartridge, where $Ca^{2+}$, $Mg^{2+}$, $K^+$, urea, creatinine and phosphate were removed. The dialysate was then reconstituted by addition of the toxin/infusate solution in order to maintain the challenge concentration of urea, creatinine and phosphate and to add $Ca^{2+}$, $Mg^{2+}$ and $K^+$. Aliquots of the dialysate were obtained via the sample port 60.

Figure 4:
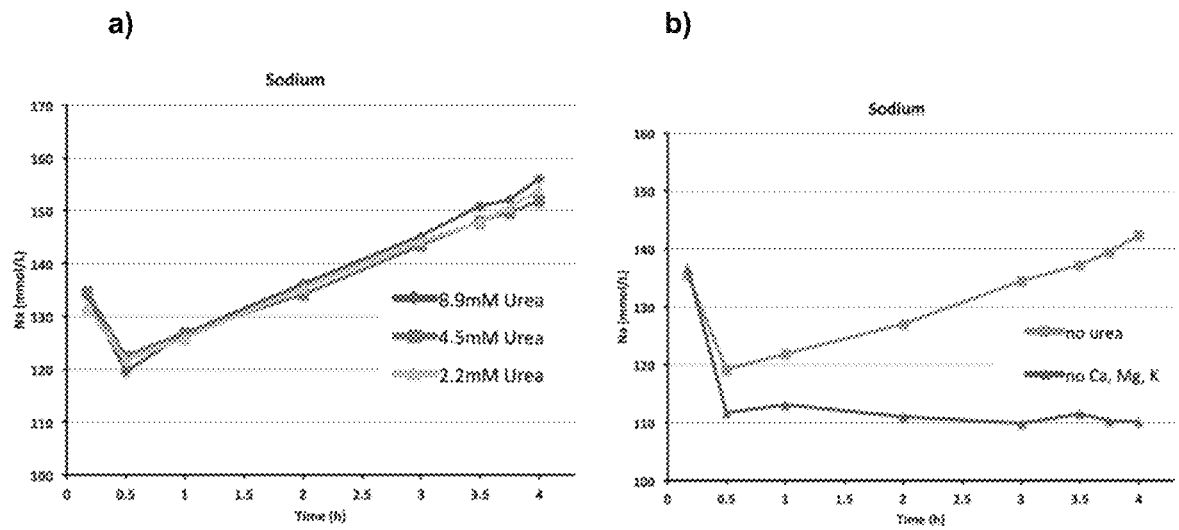
FIG. 4 is (a) a graph showing the effect of patient urea level on sodium ion concentration and (b) is a graph showing the effect of dialysate urea and Ca/Mg/K on sodium ion concentration.
Figure 7:
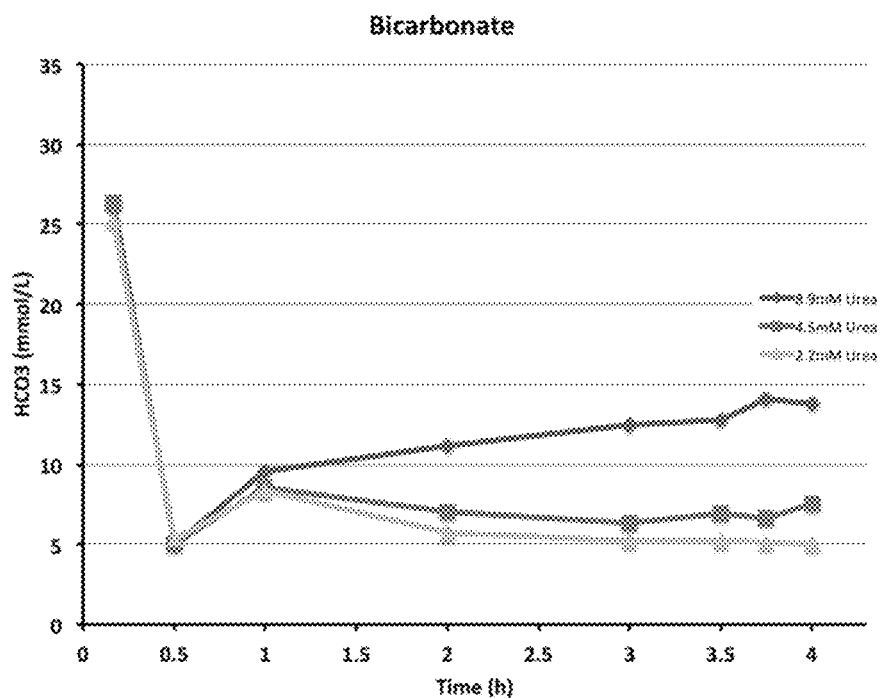
FIG. 7 is a graph showing the effect of patient urea level on carbonate concentration.
Figure 8:
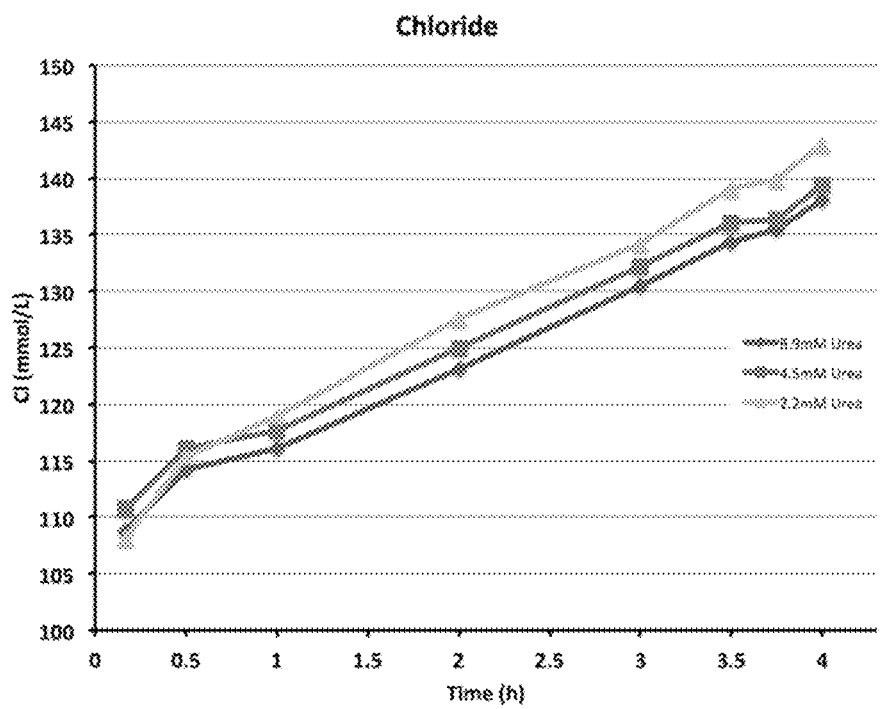
FIG. 8 is a graph showing the effect of patient urea level on chloride concentration.

The following was observed:

a) Sodium: The $Na^+$ concentration over time for all three urea concentrations showed a similar trend, indicating that the concentration of urea did not have an effect on the release of $Na^+$ from the sorbent cartridge (FIG. 4a).

b) Bicarbonate: $HCO_3^-$ profile shows only a weak dependency on the dialysate urea concentration. There is an initial loss of $HCO_3^-$ in line with the described bicarbonate drop. Subsequently, the apparent absence of a significant bicarbonate increase indicates that approximately all $NH_4^+$ formed from urea is exchanged to $H^+$, which combines with $HCO_3^-$ formed from urea and releases it as $CO_2$ (FIG. 7).

c) Chloride: $Cl^-$ profile (slope) is independent of dialysate urea concentration. There is a steady increase of $Cl^-$ from infusate addition (FIG. 8).

Example 5—Effect of $Ca^{2+}$, $Mg^{2+}$ and $K^+$, Infusion on Dialysate Chemistry In order to distinguish the dialysate effects of urea (ammonium) removal vs Ca/Mg/K removal, two identical sorbent cartridges (refer to Table 2) were challenged with dialysates containing either urea or Ca Mg and K in the recirculating miniature dialysis setup 10 described above with reference to FIG. 2. As in Example 4, in each experiment, the dialysate was pumped through the sorbent cartridge followed by the addition of an infusate to replenish and to maintain the respective concentration of $Ca^{2+}$, $Mg^{2+}$, $K^+$, urea, creatinine and phosphate of the dialysate (where relevant). Aliquots of the dialysates were obtained via sample port 60.

Figure 10:
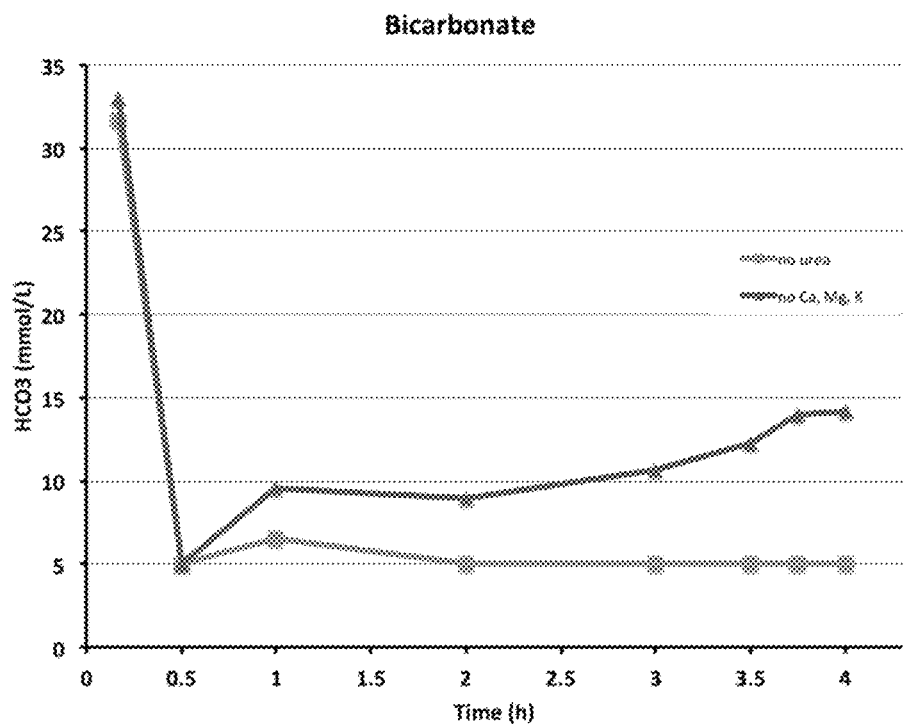
FIG. 10 is a graph showing the effect of dialysate urea and Ca/Mg/K on bicarbonate concentration.
Figure 11:
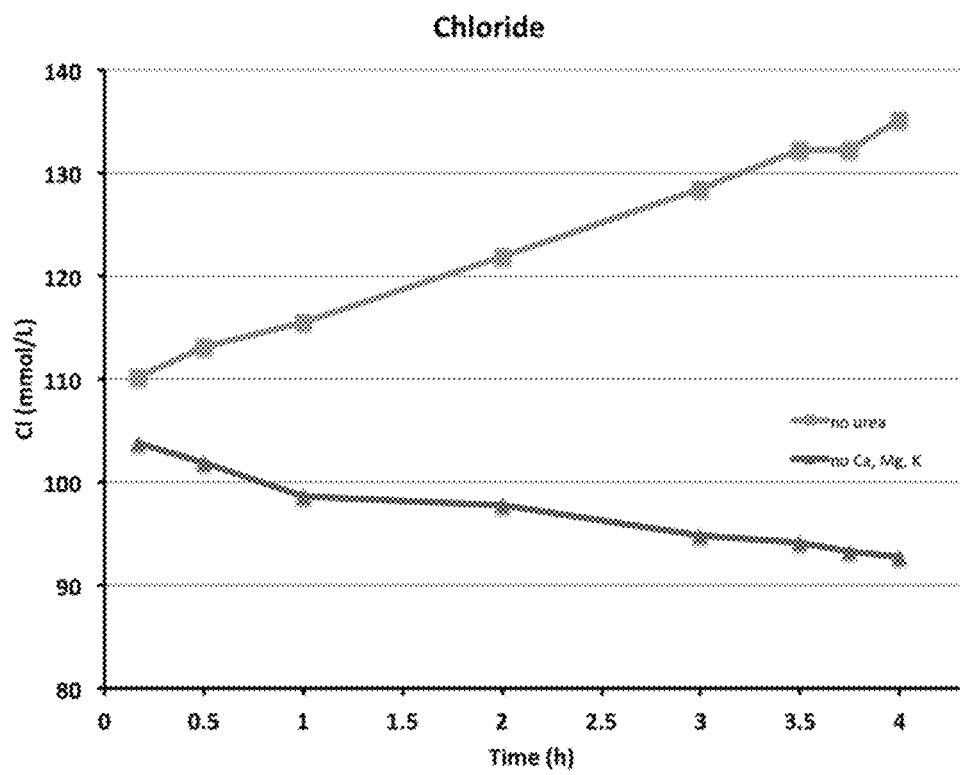
FIG. 11 is a graph showing the effect of dialysate urea and Ca/Mg/K on chloride concentration
Figure 12:
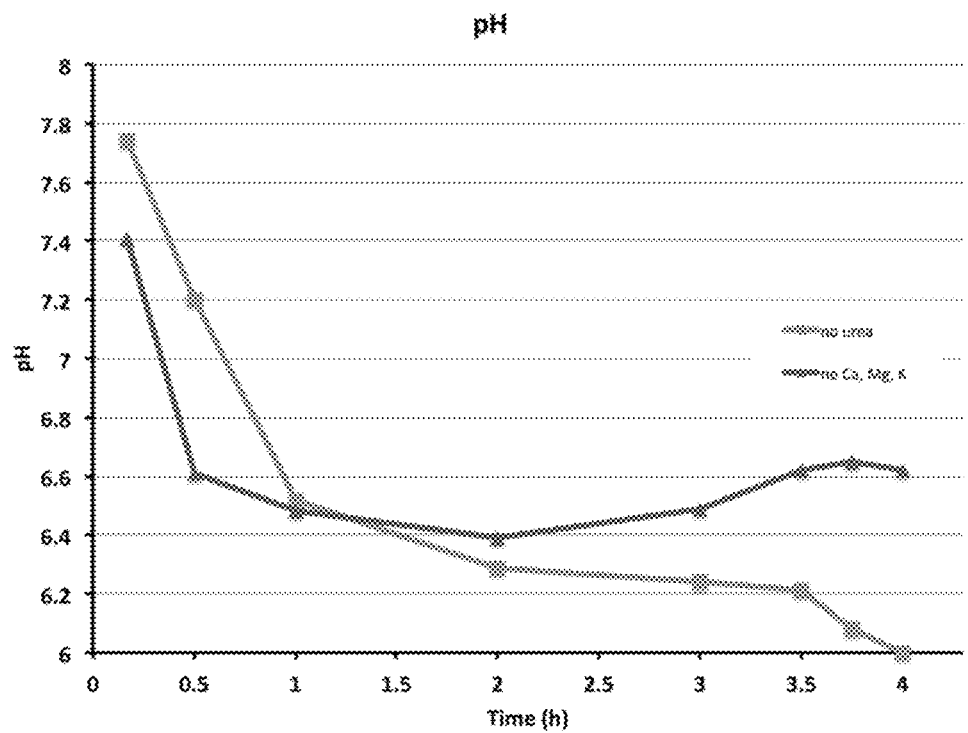
FIG. 12 is a graph showing the effect of dialysate urea and Ca/Mg/K on pH.

The following was observed:

a) Sodium: In the absence of urea, the $Na^+$ profile over time resembled the typical profile which showed an initial drop with a subsequent increase in $Na^+$ concentration over time (FIG. 4b). However, in the absence of $Ca^{2+}$, $Mg^{2+}$ and $K^+$, the $Na^+$ concentration showed a greater initial drop and it remained relatively constant thereafter (at approximately 110 mmol/L) (FIG. 4b). This shows that the increase in $Na^+$ concentration is caused by $Ca^{2+}$, $Mg^{2+}$ and $K^+$, presumably via cation exchange to displace and release the $Na^+$ from the sorbent cartridge (FIG. 4b).

b) Bicarbonate, pH, Cl: The $HCO_3^-$ profile shows only weak dependency of presence of infusate or urea. Neither binding of urea nor Ca/Mg has a significant effect on $HCO_3^-$ (FIG. 10). It was observed that $Cl^-$ increased in presence of infusate, with an approximately equal increase to the increase in $Na^+$. There was no $Cl^-$ increase in the presence of urea without infusate but a steady increase of Cl from infusate addition (FIG. 11). Thus, infusate addition formally increases NaCl concentration. Additionally, a very low pH in the presence of Ca/Mg and absence of urea was observed (FIG. 12). Acidification through formal loss of $HCO_3^-$ and increase of $Cl^-$ from infusate addition was evident.

Example 6—Improved $Na^+$ Profile after Modification

Figure 6:
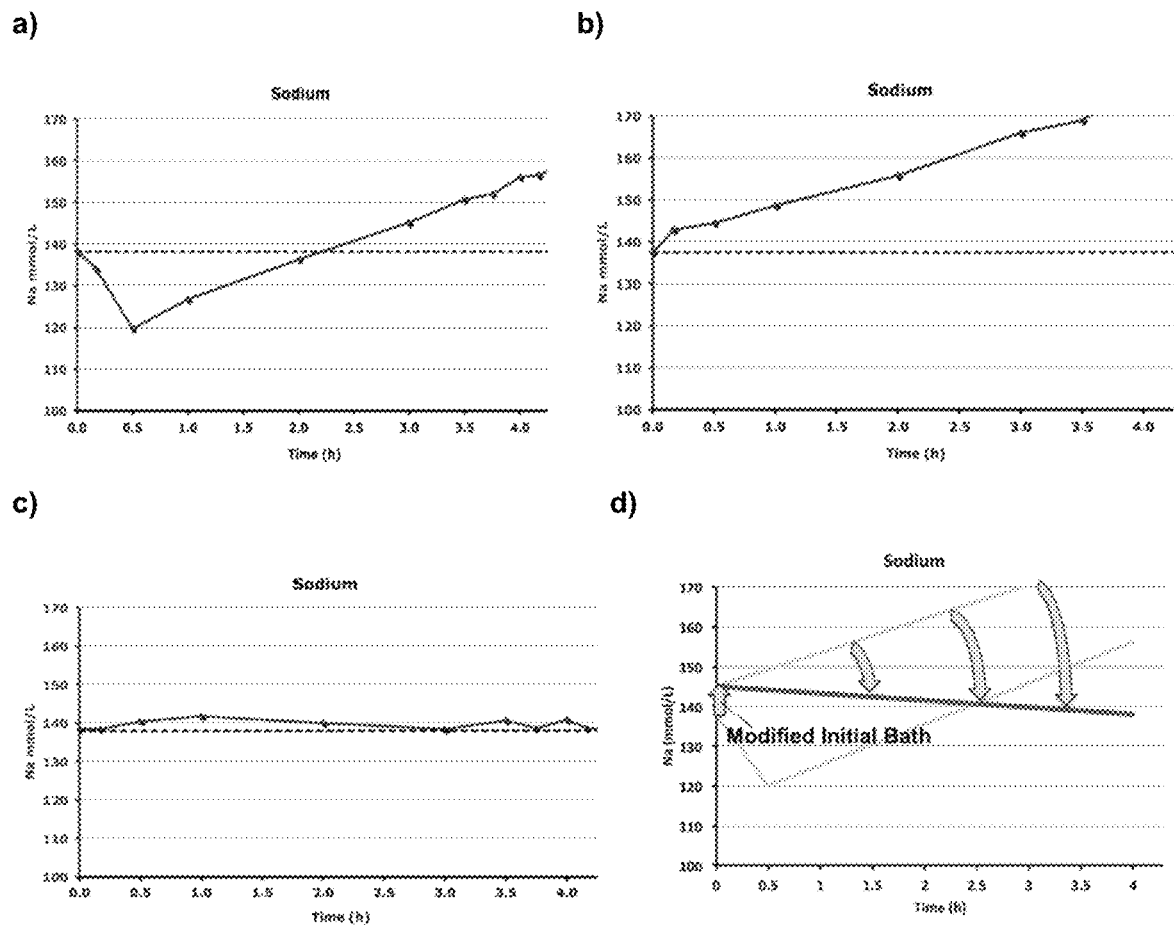
FIG. 6 is a diagram showing (a) the initial sodium drop and subsequent gradual rise in sodium concentration in conventional sorbent-based dialysis systems, (b) the effect of a sorbent modification to overcome the initial sodium drop without alteration to the gradual rise in sodium concentration, (c) the effect of system modification to address both the initial sodium drop and the subsequent gradual rise in sodium concentration to provide a steady sodium concentration throughout the dialysis, and (d) the effect of system modification to address both the initial sodium drop and the subsequent gradual rise in sodium concentration to provide a gradual reduction in sodium concentration during the dialysis.
Figure 13:
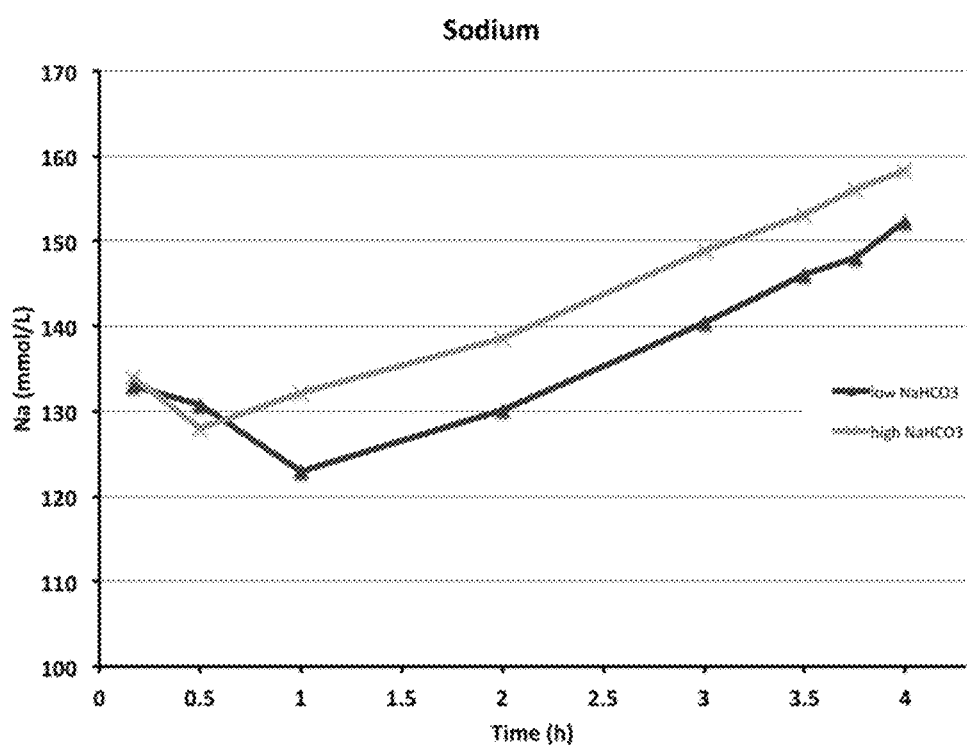
FIG. 13 is a graph showing the effect of sodium bicarbonate in the sorbent on sodium ion concentration.
Figure 14:
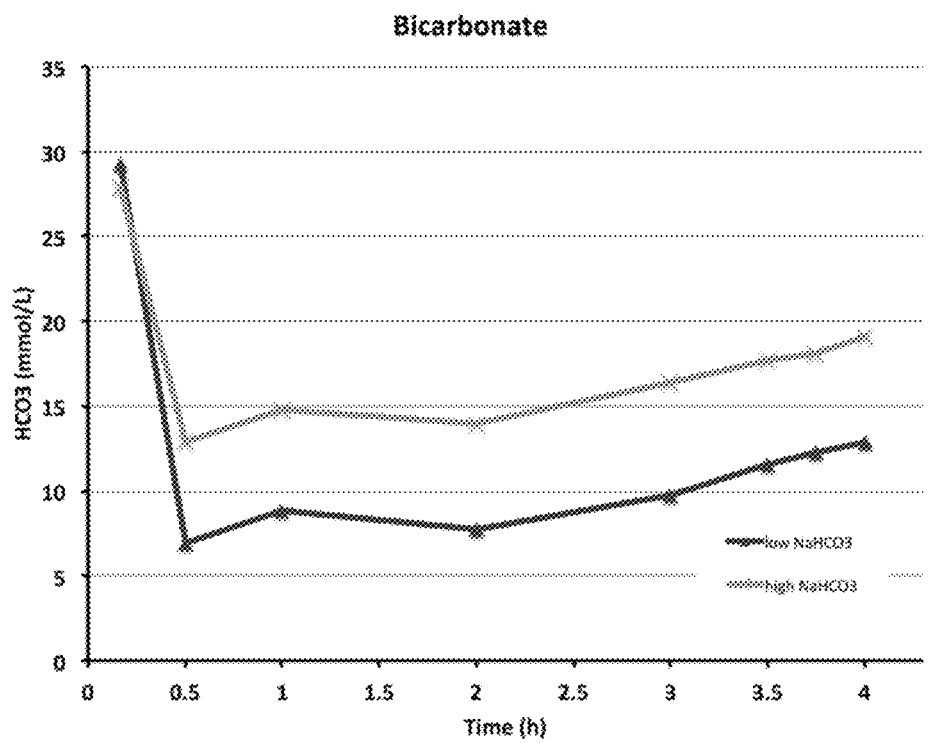
FIG. 14 is a graph showing the effect of sodium bicarbonate in the sorbent on bicarbonate concentration.

The dialysate effects of addition of soluble sodium salts to the sorbent were investigated by testing two sorbent compositions (see Table 2, Example 6) with identical dialysate and infusate solutions in the recirculating miniature dialysis setup 10 described above with reference to FIG. 2. Apart from the increase in sodium bicarbonate, the sorbents were identical in composition.

a) Sodium: An initial $Na^+$ drop is prevented, or at least reduced, by increasing the amount of (basic) $Na^+$ salt in the sorbent mixture. The slope of $Na^+$ increase during steady phase is not affected (FIG. 13). Thus, the addition of (basic) $Na^+$ salt improves or avoids the initial $Na^+$ drop apparent in conventional systems without affecting sorbent ion exchange behavior.

ent (FIG. 6c). The infusate composition was amended by increasing the infusate volume. With further modifications, it is possible to achieve a negative sodium gradient similar to sodium gradients typically applied in sodium modelling (FIG. 6d). For instance, using a pre-dialysis starting bath of Na 142 mM and performing dialysis in combination with a suitably modified infusate composition and infusion rate can produce such a result with the sorbent disclosed herein.

Example 8—Comparative Effect of HZO Modification, Soluble Sodium Salt and Infusion Conditions on Cation Exchange Efficiency

TABLE 3

Figure 15:
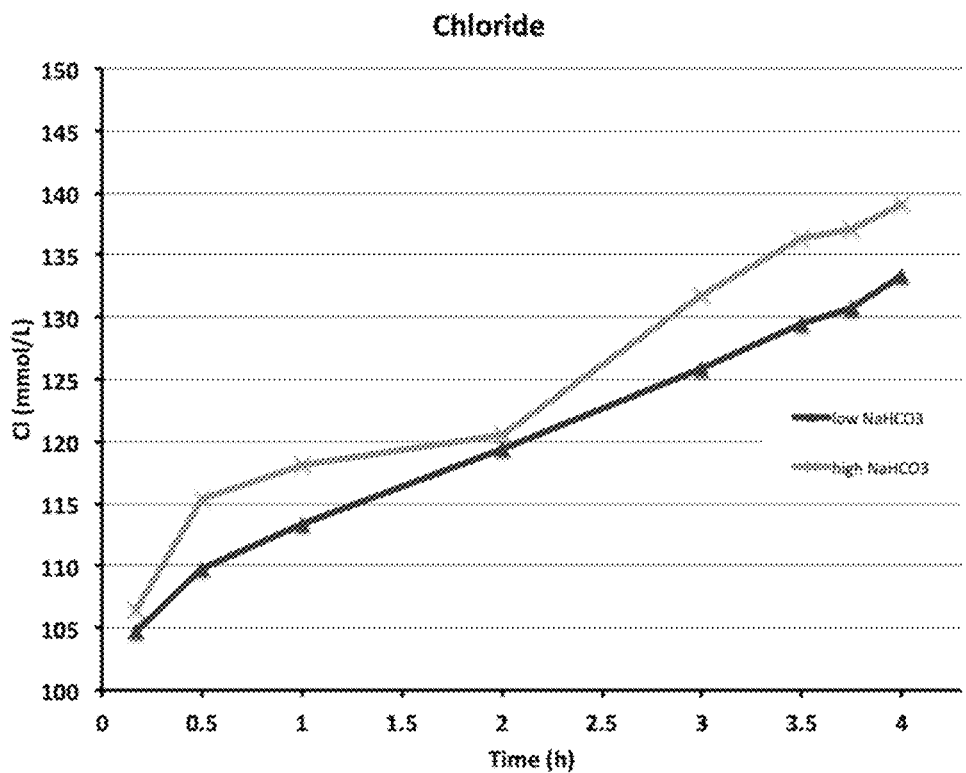
FIG. 15 is a graph showing the effect of sodium bicarbonate in the sorbent on chloride concentration.

|  | Example | | | | | | |
|---|---|---|---|---|---|---|---|
|  | 8A | 8B (repeat of 8A) | 8C | 8D | 8E | 8F | 8G |
| Urea level | 8.93 mM | 8.93 mM | 8.93 mM | 8.93 mM | 0.00 mM | 8.93 mM | 8.93 mM |
| Ca, Mg, K | Yes | Yes | Yes | No | Yes | Yes | Yes |
| ZP (g) | 40 | 40 | 40 | 40 | 40 | 40 | 40 |
| HZO - washed (g) | 17 | 17 | 17 | 17 | 17 | — | — |
| HZO - unwashed (g) | — | — | — | — | — | 17 | 17 |
| AC (g) | 8.8 | 8.8 | 8.8 | 8.8 | 8.8 | 8.8 | 8.8 |
| IU (g) | 1.0 | 1.0 | 1.0 | 1.0 | 1.0 | 1.0 | 1.0 |
| $Na_2CO_3$ (g) | — | — | — | — | — | 0.54 | 0 |
| $NaHCO_3$ (g) | 0.43 | 0.43 | 0.86 | 0.43 | 0.43 | — | 0.43 |
| Infusate vol (mL) | 30 | 30 | 30 | 30 | 30 | 30 | 30 |
| Phos source | $KH_2PO_4$ | $KH_2PO_4$ | $KH_2PO_4$ | $H_3PO_4$ | $KH_2PO_4$ | $KH_2PO_4$ | $KH_2PO_4$ |
| $NH_4^+ \to H^+$ | 94% | 96% | 94% | 94 | N/A | 88% | 90% |
| $NH_4^+ \to Na^+$ | 6% | 4% | 6% | 6% | N/A | 12% | 10% |
| $Ca^{2+}/Mg^{2+}/K^+ \to Na+$ | 94% | 90% | 85% | N/A | 83% | 94% | 94% | b) Bicarbonate: The usual initial $HCO_3^-$ drop is significantly improved by increasing the amount of (basic) $Na^+$ salt in the sorbent mix. The $HCO_3^-$ increase during steady phase is not affected, and remains at approx. zero (FIG. 13). Thus, the addition of a (basic) $Na^+$ salt reduces the initial $HCO_3^-$ drop without affecting sorbent ion exchange behavior.

c) Chloride: The $Cl^-$ profile is essentially independent of the amount of (basic) Na-salt in the sorbent mixture (FIG. 15). Thus, the addition of a (basic) $Na^+$ salt does not significantly affect the $Cl^-$ concentration.

Example 7—Modification to Sorbent and Infusate Composition to Allow Control of $Na^+$ Profile In order to advantageously utilize the concepts unveiled in Examples 4, 5 and 6 to build an intrinsically regulated sorbent dialysis system, a series of experiments were conducted with modified sorbent and infusate compositions. Three sorbent cartridges were tested in the recirculating miniature dialysis setup 10 described above with reference to FIG. 2 (see Table 2, Example 7). In the first experiment, an unmodified sorbent was used in a simulated dialysis session with unmodified infusate solution (FIG. 6a), giving the characteristic drop in sodium followed by steady increase. In the second experiment, the sorbent was modified to include additional $Na_2CO_3$ as soluble sodium salt. This corrected the drop in sodium, but the subsequent sodium gradient remained (FIG. 6b). In the third experiment, the same modified sorbent was included in the dialysis circuit with a modified infusate, whereby the infusate composition was changed to counterbalance the dialysate sodium gradi- Use of unwashed HZO (with high Na-loading) in example 8F-8G (Table 3) appeared to result in less favourable ammonium to $H^+$ exchange properties (only 88% of ammonium exchanged for $H^+$) as compared to use of washed HZO with lower Na-loading (at least 94% exchange of ammonium for $H^+$) in example 8A-8E (Table 3). This suggests that the traditional approach of sorbent modification in terms of pre-loading of ZP or HZO with Na produces results that are inferior to use of additive as in the present invention.

Example 9 Formulas to Calculate Infusate Composition and Infusion Ratio for Reconstitution Process Solution to maintain stable Na concentration:
The regenerated dialysate leaving the sorbent cartridge must be reconstituted with a solution of $Ca^{2+}/Mg^{2+}/K^+$ containing approximately 138 mEq/L of combined $Ca^{2+}/Mg^{2+}/K^+$.
In that way, the additional $Na^+$ exchanged for $Ca^{2+}/Mg^{2+}/K^+$ will be met with a volume of infusate, which will reconstitute the additional $Na^+$ to a concentration of 138 mEq/L.
In an idealised analysis, the infusate salt concentration has to fulfill the following condition $$c^I_{CaMgK} + c^I_{Na} = c^D_{Na}$$

where
$c^I_{CaMgK}$ infusate concentration of combined $Ca^{2+}/Mg^{2+}/K^+$
$c^D_{Na}$: target dialysate $Na^+$ concentration
$c^I_{Na}$: concentration of Na in infusate solution (if present)
More Detailed Analysis:

In a more detailed analysis, the infusate salt concentration must fulfill the following condition $$c^J_{CaMgK} \times \eta_{CaMgK} + c^D_{urea} \times \eta_{urea} + c^J_{Na} = c^D_{Na}$$

where $c^J_{CaMgK}$: infusate concentration of combined $Ca^{2+}/Mg^{2+}/K^+$ $c^J_{Na}$: infusate concentration of $Na^+$ (optionally added; e.g. NaCl)

$c^D_{Na}$: target dialysate $Na^+$ concentration $c^D_{urea}$: dialysate urea concentration before regeneration $\eta_{CaMgK}$: exchange efficiency $Ca^{2+}/Mg^{2+}/K^+$ to $Na^+$ (approx. 0.85-1)

$\eta_{urea}$: exchange efficiency urea to $Na^+$ (<0.1)

The optimum concentration $c^J_{CaMgK}$ and optimum infusion ratio may further be determined for the targeted dialysate composition by empirical iterative optimisation (fine-tuning)

Calculation of Infusion Ratio:

In an idealised analysis, the infusion ratio (ratio of infusate addition flow rate to regenerated dialysate flow rate) is then calculated as $$r = v^J/v^D = c^D_{CaMgK}/c^J_{CaMgK}$$

where r: infusion ratio $v^J$: Infusate addition flow rate $v^D$: regenerated dialysate flow rate $c^D_{CaMgK} = c^D_{Ca} + c^D_{Mg} + c^D_K$ target dialysate $Ca^{2+}/Mg^{2+}/K^+$ concentration $c^J_{CaMgK} = c^J_{Ca} + c^J_{Mg} + c^J_K$: infusate $Ca^{2+}/Mg^{2+}/K^+$ concentration Idealised Example $c^D_{Ca}=3$ mEq/L $c^D_{Mg}=1$ mEq/L $c^D_K=3$ mEq/L $c^D_{CaMgK}=7$ mEq/L $c^D_{Na}=138$ mEq/L $c^J_{CaMgK}=c^J_{Na}=138$ mEq/L $r=c^D_{CaMgK}/c^J_{CaMgK}=7$ mEq/L/138 mEq/L≈1:20

Figure 16:
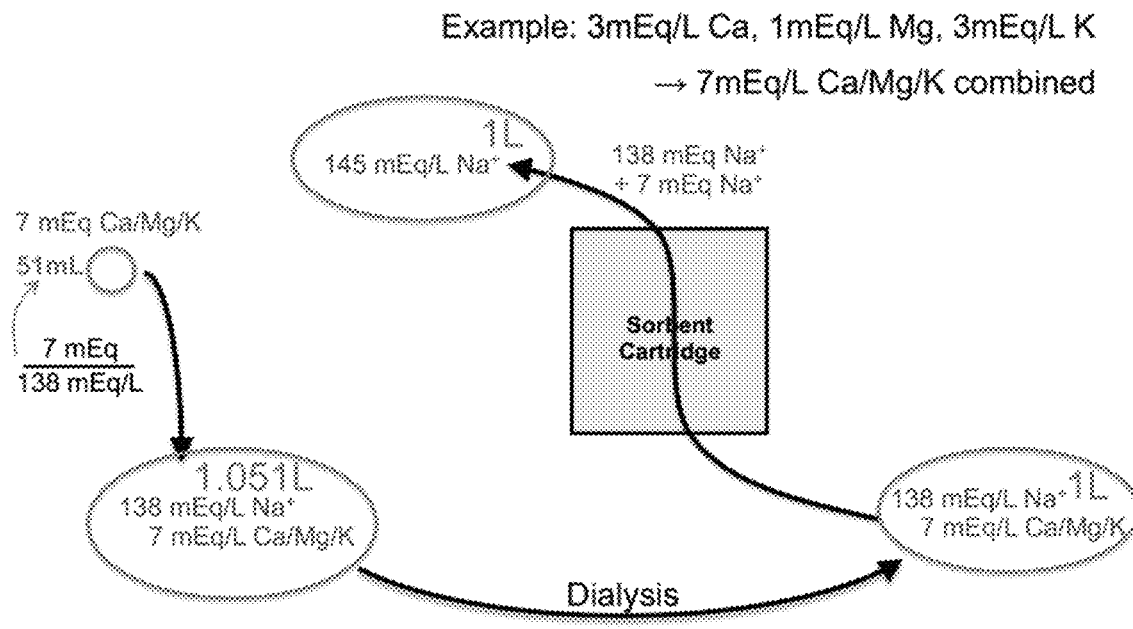
FIG. 16 is a diagram illustrating a dialysis process in accordance with the present invention.

An example of the dialysis reconstitution process is illustrated in FIG. 16. In the example illustrated the infusate solution is 51 mL in volume and includes 3 mEq/L Ca, 1 mEq/L Mg, 3 mEq/L K.

Additional Examples with and without Addition of NaCl:

A target dialysate composition $c^D_{Ca}=3$ mEq/L $c^D_{Mg}=1$ mEq/L $c^D_K=3$ mEq/L $c^D_{Na}=138$ mEq/L may be achieved by infusing the following solution at an infusion ratio of 1:20

$c^J_{Ca}=59$ mEq/L $c^J_{Mg}=20$ mEq/L $c^J_K=59$ mEq/L $c^J_{Na}=0$ mEq/L

Figure 5:
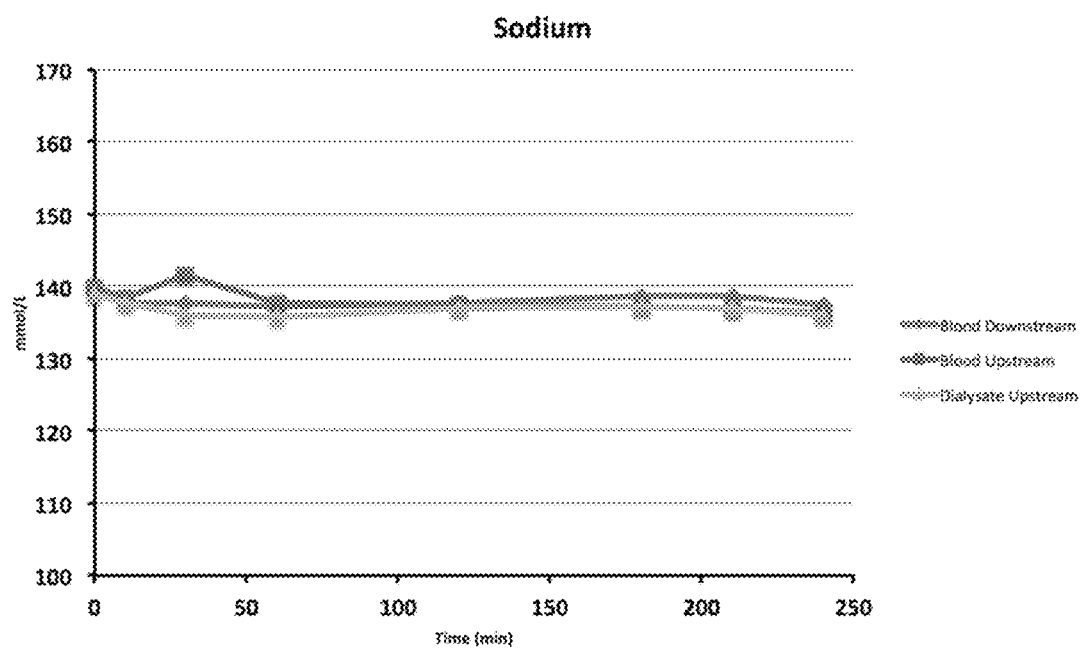
FIG. 5 is a graph showing the sodium concentration of simulated patient biological fluid before and after purification in a double loop dialysis system ("Blood Upstream" and "Blood Downstream"), as well as the sodium concentration in regenerated and reconstituted dialysate ("Dialysate Upstream") according to the present invention.

The same infusion ratio can be used to produce a dialysate containing $c^D_{Ca}=2.5$ mEq/L $c^D_{Mg}=1$ mEq/L $c^D_K=2$ mEq/L $c^D_{Na}=138$ mEq/L if an infusate of the following composition is used $c^J_{Ca}=49$ mEq/L $c^J_{Mg}=20$ mEq/L $c^J_K=39$ mEq/L $c^J_{Na}=30$ mEq/L Example 10: Full Scale In Vitro Experiment A full scale experiment according to dialysis circuit 110 shown in FIG. 3 was conducted on a simulated patient of 40 L simulated body fluid. The sorbent composition consisted of the following materials: ZP (1141 g), washed HZO (472 g), AC (160 g), IU (27 g) and sodium carbonate (50 g). The sorbent was dry packed into a container consisting a cylindrical compartment with inlet and outlet, with filter papers installed before and after the sorbent layer. An infusate volume of 4 L was infused over 4 h, containing enough salts to reconstitute 72 L of regenerated dialysate during dialysis. The dialysis session was conducted according to the parameters in Table 1. The infusion flow rate was 16.7 mL/min and the dialyate flow rate was 300 mL/min. A blood circuit flow rate of 300 mL/min and a simulated blood toxin concentration approximately 1.5 times (assumption of approx. 60% total toxin transfer from the simulated patient body fluid to dialysate) the value stated in the description was used in order to deliver the required toxin challenge to the cartridge in the dialysate circuit. The simulated patient solution thus contained 964.5 mmol urea, 40.4 mmol creatinine and 137.4 mmol phosphate in 40 L of simulated body fluid. Blood upstream of the dialyser was sampled at "blood in", blood downstream at "blood out" and likewise for the dialysate circuit. As a result of the intrinsic regulation through modified sorbent and infusate compositions, a stable sodium concentration was observed in both the blood and dialysate circuits for the duration of the dialysis session (FIG. 5).

Statements of Invention

1. A sorbent for removing metabolic waste products from a dialysis liquid, the sorbent comprising a soluble source of sodium ions.

2. A sorbent as described in statement 1 wherein the soluble source of sodium ions is a soluble salt.

3. A sorbent as described in statement 2 wherein the soluble salt is a basic salt.

4. A sorbent as described in statement 3 wherein the soluble salt is selected from one or more of the group consisting of sodium carbonate, sodium bicarbonate and sodium hydroxide.

5. A sorbent as described in statement 4 wherein the soluble salt is sodium bicarbonate.

6. A sorbent as described in statement 2 wherein the soluble salt is a neutral salt.

7. A sorbent as described in statement 6 wherein the sodium salt is sodium chloride.

8. A sorbent as described in statement 2 wherein the soluble salt is a salt of a weak acid.

9. A sorbent as described in statement 8 wherein the soluble salt is sodium lactate or sodium acetate.

10. A sorbent as described in any one of statements 1 to 9, the sorbent comprising a soluble source of sodium ions in homogeneous mixture with at least one of: (a) uremic toxin-treating enzyme particles comprising a uremic toxin-treating enzyme immobilized on a solid support; (b) cation exchange particles configured to exchange ammonium ions for predominantly hydrogen ions and to exchange essential cations predominantly for sodium ions; and (c) anion exchange particles.

11. A sorbent as described in statement 10 wherein said cation exchange particles are set to a pH in the range of from 3.5 to 5.0.

12. A sorbent as described in statement 11 wherein said cation exchange particles are set to a pH of about 4.5.

13. A sorbent as described in any one of statements 10 to 12 wherein said cation exchange particles have a particle size in the range of from 10 to 1000 microns, preferably of from 25 to 150 microns, more preferably of from 50 to 100 microns.

14. A sorbent as described in any one of statements 10 to 13 wherein said cation exchange particles comprise an amorphous, water-insoluble metal phosphate in partially protonated form.

15. A sorbent as described in statement 14 wherein the metal is selected from the group consisting of titanium, zirconium, hafnium and combinations thereof.

16. A sorbent as described in statement 15 wherein the metal is zirconium.

17. A sorbent as described in any one of statements 10 to 16 wherein said anion exchange particles are set to a pH in the range of from 7 to 14, preferably from 12 to 13.

18. A sorbent as described in any one of statements 10 to 17 wherein said anion exchange particles are saturated with a base.

19. A sorbent as described in statement 18 wherein the base is selected from the group consisting of sodium hydroxide, sodium carbonate, sodium bicarbonate, potassium hydroxide, magnesium hydroxide; calcium hydroxide, ammonium carbonate and ammonium hydroxide.

20. A sorbent as described in statement 19 wherein the base is sodium hydroxide.

21. A sorbent as described in any one of statements 10 to 20, wherein said anion exchange particles comprise an amorphous and partly hydrated, water-insoluble metal oxide in its hydroxide-, carbonate-, acetate-, and/or lactate-counter-ion form, wherein the metal may be selected from the group consisting of titanium, zirconium, hafnium and combinations thereof.

22. A sorbent as described in statement 21 wherein the anion exchange particles are zirconium oxide particles.

23. A sorbent as described in statement 22 wherein the anion exchange particles are hydrous zirconium oxide particles.

24. A sorbent as described in any one of statements 10 to 23 wherein said anion exchange particles have a particle size in the range of from 10 to 1000 microns, preferably of from 25 to 150 microns, more preferably of from 50 to 100 microns.

25. A sorbent as described in any one of statements 10 to 24 wherein the ratio of cation exchange particle to anion exchange particle is in the range of from 1:1 to 5:1.

26. A sorbent as described in statement 25 wherein the ratio of cation exchange particle to anion exchange particle is in the range of 2:1 to 3:1.

27. A sorbent as described in statement 26 wherein the ratio of cation exchange particle to anion exchange particle is about 2.4:1.

28. A sorbent as described in any one of statements 10 to 26, wherein said uremic toxin-treating enzyme particles comprise a urease.

29. A sorbent as described in any one of statements 10 to 28, wherein said uremic toxin-treating enzyme particles have an average particle size in the range of from 10 microns to 1000 microns.

30. A sorbent as described in any one of statements 10 to 29, further comprising organic compounds absorber particles.

31. A sorbent as described in statement 30, wherein said organic compounds absorber particles are activated carbon particles.

32. A sorbent as described in statement 31, wherein said activated carbon particles have an average particle size in the range of from 10 microns to 1000 microns.

33. A sorbent as described in any one of statements 10 to 32 further comprising a carbonic anhydrase.

34. A sorbent for removing metabolic waste products from a dialysis liquid, the sorbent comprising a homogeneous mixture of: (a) uremic toxin-treating enzyme particles comprising a uremic toxin-treating enzyme immobilized on a solid support; (b) cation exchange particles configured to exchange ammonium ions for predominantly hydrogen ions and to exchange essential cations predominantly for sodium ions; and (c) anion exchange particles, and further comprising a soluble source of sodium ions.

35. A sorbent as described in statement 34 wherein the soluble source of sodium ions is a soluble salt.

36. A sorbent as described in statement 35 wherein the soluble salt is a basic salt.

37. A sorbent as described in statement 36 wherein the soluble salt is selected from one or more of the group consisting of sodium carbonate, sodium bicarbonate and sodium hydroxide.

38. A sorbent as described in statement 37 wherein the soluble salt is sodium bicarbonate.

39. A sorbent as described in statement 35 wherein the soluble salt is a neutral salt.

40. A sorbent as described in statement 39 wherein the sodium salt is sodium chloride.

41. A sorbent as described in statement 35 wherein the soluble salt is a salt of a weak acid.

42. A sorbent as described in statement 41 wherein the soluble salt is sodium lactate or sodium acetate.

43. A sorbent as described in any one of statements 34 to 42 wherein said cation exchange particles are set to a pH in the range of from 3.5 to 5.0.

44. A sorbent as described in statement 43 wherein said cation exchange particles are set to a pH of about 4.5.

45. A sorbent as described in any one of statements 34 to 44 wherein said cation exchange particles have a particle size in the range of from 10 to 1000 microns, preferably of from 25 to 150 microns, more preferably of from 50 to 100 microns.

46. A sorbent as described in any one of statements 34 to 45 wherein said cation exchange particles comprise an amorphous, water-insoluble metal phosphate in partially protonated form.

47. A sorbent as described in statement 46 wherein the metal is selected from the group consisting of titanium, zirconium, hafnium and combinations thereof.

48. A sorbent as described in statement 47 wherein the metal is zirconium.

49. A sorbent as described in any one of statements 34 to 48 wherein said anion exchange particles are set to a pH in the range of from 7 to 14, preferably from 12 to 13.

50. A sorbent as described in any one of statements 34 to 49 wherein said anion exchange particles are saturated with a base.

51. A sorbent as described in statement 50 wherein the base is selected from the group consisting of sodium hydroxide, sodium carbonate, sodium bicarbonate, potassium hydroxide, magnesium hydroxide; calcium hydroxide, ammonium carbonate and ammonium hydroxide.

52. A sorbent as described in statement 51 wherein the base is sodium hydroxide.

53. A sorbent as described in any one of statements 34 to 52, wherein said anion exchange particles comprise an amorphous and partly hydrated, water-insoluble metal oxide in its hydroxide-, carbonate-, acetate-, and/or lactate-counter-ion form, wherein the metal may be selected from the group consisting of titanium, zirconium, hafnium and combinations thereof.

54. A sorbent as described in statement 53 wherein the anion exchange particles are zirconium oxide particles.

55. A sorbent as described in statement 54 wherein the anion exchange particles are hydrous zirconium oxide particles.

56. A sorbent as described in any one of statements 34 to 55 wherein said anion exchange particles have a particle size in the range of from 10 to 1000 microns, preferably of from 25 to 150 microns, more preferably of from 50 to 100 microns.

57. A sorbent as described in any one of statements 34 to 56 wherein the ratio of cation exchange particle to anion exchange particle is in the range of from 1:1 to 5:1.

58. A sorbent as described in statement 57 wherein the ratio of cation exchange particle to anion exchange particle is in the range of 2:1 to 3:1.

59. A sorbent as described in statement 58 wherein the ratio of cation exchange particle to anion exchange particle is about 2.4:1.

60. A sorbent as described in any one of statements 34 to 59, wherein said uremic toxin-treating enzyme particles comprise a urease.

61. A sorbent as described in any one of statements 34 to 60, wherein said uremic toxin-treating enzyme particles have an average particle size in the range of from 10 microns to 1000 microns.

62. A sorbent as described in any one of statements 34 to 60, further comprising organic compounds absorber particles.

63. A sorbent as described in statement 62, wherein said organic compounds absorber particles are activated carbon particles.

64. A sorbent as described in statement 63, wherein said activated carbon particles have an average particle size in the range of 10 microns to 1000 microns.

65. A sorbent as described in any one of statements 34 to 64 further comprising a carbonic anhydrase.

66. A process of preparing a sorbent comprising mixing a soluble source of sodium ions and at least one of: (a) uremic toxin-treating enzyme particles comprising a uremic toxin-treating enzyme immobilized on a solid support; (b) cation exchange particles configured to exchange ammonium ions for predominantly hydrogen ions and to exchange essential cations for sodium ions; (c) anion exchange particles; and (d) organic compounds absorber particles, and containing the mixture.

67. A sorbent which hydrolyses urea to ammonium and bicarbonate, and binds ammonium predominantly in exchange for protons.

68. A sorbent which predominantly binds essential cations in exchange for sodium ions.

69. A sorbent which (a) hydrolyses urea to ammonium and bicarbonate, and (b) binds ammonium predominantly in exchange for protons and binds essential cations predominantly in exchange for sodium ions.

70. A sorbent cartridge comprising a sorbent as described in any one of statements 1 to 69 contained within a cartridge.

71. A dialysis system for treating and recycling dialysate, the system comprising a sorbent cartridge as described in any one of statements 1 to 69 which releases a predicted amount of sodium following ion exchange in the sorbent, a conduit for conveying spent dialysate from a source of spent dialysate to the sorbent cartridge, a conduit for conveying regenerated dialysate from the sorbent cartridge to the source of spent dialysate, and an infusate system for dosing an infusate solution comprising essential cations to the regenerated dialysate such that the solution combines with the predicted release of sodium ions from the sorbent cartridge to generate a predetermined dialysate sodium concentration.

72. A dialysis system as described in statement 71 wherein the essential cations are divalent cations and/or potassium ions.

73. A dialysis system as described in statement 72 wherein the divalent cations are calcium and/or magnesium ions.

74. A dialysis system as described in any one of statements 71 to 73 adapted to keep sodium ion concentration constant in the dialysate.

75. A dialysis system as described in statement 74 adapted to produce a concentration of sodium ions of from 132 mEq/L to 145 mEq/L.

76. A dialysis system as described in any one of statements 71 to 73 adapted to reduce sodium ion content in regenerated dialysate.

77. A dialysis system as described in any one of statements 71 to 76 further comprising a source of an osmotic agent for addition to the regenerated dialysate.

78. A dialysis system as described in any one of statements 71 to 77 further comprising a source of salts other than calcium, magnesium and potassium salts for addition to the regenerated dialysate.

79. A dialysis system as described in statements 78 wherein the salt other than a calcium, magnesium and potassium salt is sodium chloride.

80. A dialysis system as described in any one of statements 71 to 79 wherein the pH of the regenerated dialysate is maintained within a range of 6 to 8

81. A process for regenerating dialysate in a dialysis process, comprising repeating the steps of:
(a) conveying spent dialysate from a source of spent dialysate to a sorbent which (a) hydrolyses urea to ammonium and bicarbonate, and (b) binds ammonium predominantly in exchange for protons and binds essential cations predominantly in exchange for sodium ions, to produce regenerated dialysate;
(b) introducing essential cations to the regenerated dialysate to reconstitute the dialysate; and
(c) conveying reconstituted dialysate from the sorbent to the source of spent dialysate; characterised in that a predetermined concentration of sodium ions is generated following ion exchange in the sorbent.

82. A process as described in statement 81 wherein the sorbent is a sorbent as described in any one of statements 1 to 65 or 69.

83. A sorbent which (a) hydrolyses urea to ammonium and bicarbonate, and (b) binds ammonium predominantly in exchange for protons and binds essential cations predominantly in exchange for sodium ions, to produce regenerated dialysate for use in regenerating dialysate in a dialysis process.

84. A kit comprising a sorbent as described in any one of statements 1 to 33, 34, or 38 and an infusate comprising salts of essential ions.

85. A sorbent as described in either one of statements 4 or 37 wherein the soluble salt is sodium carbonate.

86. A sorbent as described in any one of statements 1 to 9 wherein the soluble sodium salt comprises a separate layer or a compartment in the sorbent.

87. A sorbent described in either one of statements 33 or 65 wherein the carbonic anhydrase is immobilised by chemical or physical bonding to a solid support, or immobilised by cross-linking or encapsulation.

88. A dialysis system as described in statement 74 adapted to produce a concentration of sodium ions of from 120 mEq/L to 150 mEq/L.

89. A dialysis system as described in statement 71 wherein the concentration of-cation equivalents in the infusate solution is approximately equal to a predetermined dialysate sodium ion concentration so that ion exchange in the sorbent, followed by addition of the infusate solution provides a target dialysate sodium concentration.

90. A process as described in statement 81 wherein the essential cations are introduced as an infusate solution and the concentration of cation equivalents in the infusate solution is approximately equal to a predetermined dialysate sodium ion concentration so that ion exchange in the sorbent, followed by addition of the infusate solution provides a target dialysate sodium concentration.

91. A kit as described in claim 84 wherein the infusate is in the form of an infusate solution in which the concentration of essential cations is approximately equal to a target sodium ion concentration or the kit includes instructions to prepare an infusate solution in which the concentration of essential cations is approximately equal to a target sodium ion concentration.

The invention claimed is:

1. A sorbent for removing metabolic waste products from a dialysis liquid, the sorbent comprising a homogeneous mixture of:
   (a) uremic toxin-treating enzyme particles comprising a uremic toxin-treating enzyme immobilized on a solid support;
   (b) cation exchange particles configured to exchange ammonium ions for hydrogen ions and to exchange calcium, magnesium, and/or potassium cations for sodium ions such that at least 80% of exchanged ammonium ions are exchanged for hydrogen ions, and at least 80% of exchanged calcium, magnesium, and/or potassium cations are exchanged for sodium ions; and
   (c) anion exchange particles, and further comprising a soluble source of sodium ions, wherein the cation exchange particles are set to a pH range of from 3.5 to 5.0.

2. A sorbent as claimed in claim 1 wherein the soluble source of sodium ions is a soluble salt.

3. A sorbent as claimed in claim 2 wherein the soluble salt is a basic salt.

4. A sorbent as claimed in claim 3 wherein the soluble salt is selected from one or more of the group consisting of sodium carbonate, sodium bicarbonate and sodium hydroxide.

5. A sorbent as claimed in claim 1 wherein said cation exchange particles are set to a pH of 4.5.

6. A sorbent as claimed in claim 1 wherein said cation exchange particles comprise an amorphous, water-insoluble metal phosphate in protonated form.

7. A sorbent as claimed in claim 1, wherein said anion exchange particles comprise an amorphous and partly hydrated, water-insoluble metal oxide in its hydroxide-, carbonate-, acetate-, and/or lactate-counter-ion form, wherein the metal may be selected from the group consisting of titanium, zirconium, hafnium and combinations thereof.

8. A dialysis system for treating and recycling dialysate, the system comprising a sorbent as described in claim 1, which releases a predicted amount of sodium following ion exchange in the sorbent, a conduit for conveying spent dialysate from a source of spent dialysate to the sorbent, a conduit for conveying regenerated dialysate from the sorbent to the source of spent dialysate, and an infusate system for dosing an infusate solution comprising essential cations to the regenerated dialysate such that the solution combines with the predicted release of sodium ions from the sorbent cartridge to generate a predetermined dialysate sodium concentration.

* * * * *